United States Patent
Waxman et al.

(10) Patent No.: US 10,976,245 B2
(45) Date of Patent: Apr. 13, 2021

(54) SYSTEMS AND METHODS FOR LEAK MONITORING VIA MEASUREMENT OF OPTICAL ABSORPTION USING TAILORED REFLECTOR INSTALLMENTS

(71) Applicant: MultiSensor Scientific, Inc., Cambridge, MA (US)

(72) Inventors: Allen M. Waxman, Newton, MA (US); Stefan Bokaemper, Newton, MA (US); Terrence K. Jones, Sharon, MA (US); Claude V. Robotham, Somerville, MA (US)

(73) Assignee: MultiSensor Scientific, Inc., Cambridge, MA (US)

(*) Notice: Subject to any disclaimer, the term of this patent is extended or adjusted under 35 U.S.C. 154(b) by 0 days.

(21) Appl. No.: 16/413,272

(22) Filed: May 15, 2019

(65) Prior Publication Data

US 2020/0240906 A1 Jul. 30, 2020

Related U.S. Application Data

(60) Provisional application No. 62/797,065, filed on Jan. 25, 2019.

(51) Int. Cl.
*G01N 21/359* (2014.01)
*G01N 21/3504* (2014.01)

(52) U.S. Cl.
CPC ....... *G01N 21/359* (2013.01); *G01N 21/3504* (2013.01); *G01N 2201/061* (2013.01); *G01N 2201/0636* (2013.01)

(58) Field of Classification Search
CPC ............. G01N 21/359; G01N 21/3504; G01N 2201/061; G01N 21/0636
See application file for complete search history.

(56) References Cited

U.S. PATENT DOCUMENTS 3,517,190 A * 6/1970 Astheimer ............. G01N 21/53
250/339.13
3,662,171 A 5/1972 Brengman et al.
(Continued)

FOREIGN PATENT DOCUMENTS

CN 1479866 A 3/2004
CN 101680833 A 3/2010
(Continued)

OTHER PUBLICATIONS

Benson, R. et al., Standoff passive optical leak detection of volatile organic compounds using a cooled InSb based infrared imager, Proceedings of the Air & Waste Management Assoc. Conf. Extended Abstract No. 06-A-131-AQMA, pp. 1-10 (2006).
(Continued)

*Primary Examiner* — Blake C Riddick
(74) *Attorney, Agent, or Firm* — William R. Haulbrook; Ronen Adato; Choate, Hall & Stewart LLP

(57) ABSTRACT

Presented herein are systems and methods directed to a multispectral absorption-based imaging approach that provides for rapid and accurate detection, localization, and quantification of gas emission from within a site to be monitored. The imaging technology described herein utilizes an optical sensor and broadband illumination in combination with specialized reflector installments mounted about the site. The optical sensor detects light (e.g., reflected) from a plurality of sampled locations along the reflector installment, for example by imaging multiple sampled locations at a time and/or scanning an instantaneous field of view (ifov) of the optical sensor. Lines-of-sight from the optical sensor to sampled locations along the reflector installment sweep out an "optical curtain" partially enclosing and/or forming a boundary near various assets to be monitored. Optical absorption signatures from leaking gas
(Continued)

crossing the optical curtain can be used to detect, localize, and obtain quantitative measures characterizing the leak.

39 Claims, 26 Drawing Sheets
(20 of 26 Drawing Sheet(s) Filed in Color)

(56) References Cited

U.S. PATENT DOCUMENTS

| | | | | |
|---|---|---|---|---|
| 4,264,209 | A * | 4/1981 | Brewster | G01N 33/0047 250/343 |
| 4,490,613 | A | 12/1984 | Brame | |
| 4,543,481 | A | 9/1985 | Zwick | |
| 4,555,627 | A * | 11/1985 | McRae, Jr. | G01M 3/38 250/330 |
| 4,864,127 | A | 9/1989 | Brame | |
| 4,999,498 | A * | 3/1991 | Hunt | G01J 3/453 250/338.1 |
| 5,103,675 | A | 4/1992 | Komninos | |
| 5,281,816 | A | 1/1994 | Jacobson et al. | |
| 5,306,913 | A | 4/1994 | Noack et al. | |
| 5,656,813 | A | 8/1997 | Moore et al. | |
| 6,061,141 | A * | 5/2000 | Goldenberg | G01N 21/3504 356/437 |
| 6,680,778 | B2 | 1/2004 | Hinnrichs et al. | |
| 6,690,472 | B2 | 2/2004 | Kulp et al. | |
| 7,075,653 | B1 | 7/2006 | Rutherford | |
| 7,486,399 | B1 | 2/2009 | Reichardt et al. | |
| 7,649,174 | B2 | 1/2010 | Mammen et al. | |
| 7,977,639 | B2 | 7/2011 | Maillart et al. | |
| 8,193,496 | B2 | 6/2012 | Furry | |
| 8,426,813 | B2 | 4/2013 | Furry | |
| 8,730,477 | B2 | 5/2014 | Ruhland et al. | |
| 9,228,938 | B2 | 1/2016 | Hager et al. | |
| 9,955,910 | B2 | 5/2018 | Fright et al. | |
| 10,031,040 | B1 | 7/2018 | Smith et al. | |
| 10,190,976 | B2 | 1/2019 | Waxman et al. | |
| 10,197,470 | B2 | 2/2019 | Waxman et al. | |
| 10,330,593 | B1 * | 6/2019 | Dobler | G01N 21/27 |
| 10,371,627 | B2 | 8/2019 | Waxman et al. | |
| 10,436,710 | B2 | 10/2019 | Waxman et al. | |
| 2002/0071122 | A1 | 6/2002 | Kulp et al. | |
| 2004/0051043 | A1 | 3/2004 | Kilian et al. | |
| 2006/0202122 | A1 | 9/2006 | Gunn et al. | |
| 2006/0203248 | A1 | 9/2006 | Reichardt et al. | |
| 2009/0296202 | A1 * | 12/2009 | Wei | G02B 5/128 359/359 |
| 2010/0127173 | A1 * | 5/2010 | Schmidt | G01M 3/38 250/338.5 |
| 2010/0231722 | A1 | 9/2010 | Hill, Jr. et al. | |
| 2010/0241361 | A1 | 9/2010 | Hofvander et al. | |
| 2012/0062697 | A1 | 3/2012 | Treado et al. | |
| 2012/0062740 | A1 | 3/2012 | Treado et al. | |
| 2013/0118339 | A1 * | 5/2013 | Lee | G10H 1/34 84/725 |
| 2013/0248673 | A1 * | 9/2013 | Townsend, Jr. | F21V 21/008 248/327 |
| 2013/0327942 | A1 | 12/2013 | Silny | |
| 2014/0002667 | A1 | 1/2014 | Cheben et al. | |
| 2014/0008526 | A1 | 1/2014 | Zeng et al. | |
| 2014/0104607 | A1 | 4/2014 | Treado et al. | |
| 2014/0118722 | A1 | 5/2014 | Treado et al. | |
| 2014/0160479 | A1 | 6/2014 | Hager et al. | |
| 2014/0268104 | A1 | 9/2014 | Treado et al. | |
| 2015/0069239 | A1 | 3/2015 | Kester et al. | |
| 2015/0316473 | A1 | 11/2015 | Kester et al. | |
| 2015/0323449 | A1 | 11/2015 | Jones et al. | |
| 2016/0037144 | A1 * | 2/2016 | Schultz | H04N 9/3194 348/745 |
| 2016/0069743 | A1 | 3/2016 | McQuilkin et al. | |
| 2016/0097713 | A1 | 4/2016 | Kester et al. | |
| 2016/0131576 | A1 | 5/2016 | Cabib et al. | |
| 2016/0334538 | A1 * | 11/2016 | Rieker | G01N 21/3504 |
| 2016/0345835 | A1 | 12/2016 | Darty | |
| 2016/0349228 | A1 | 12/2016 | Kester et al. | |
| 2017/0108874 | A1 * | 4/2017 | Peters | G05D 1/0246 |
| 2017/0234761 | A1 | 8/2017 | Augusto | |
| 2017/0284891 | A1 | 10/2017 | Miranda | |
| 2017/0336281 | A1 | 11/2017 | Waxman et al. | |
| 2017/0336320 | A1 * | 11/2017 | Yalin | G01N 21/3504 |
| 2018/0045596 | A1 | 2/2018 | Prasad et al. | |
| 2018/0131449 | A1 * | 5/2018 | Kare | H01S 5/0085 |
| 2018/0266944 | A1 | 9/2018 | Waxman et al. | |
| 2019/0137390 | A1 | 5/2019 | Waxman et al. | |
| 2019/0145891 | A1 | 5/2019 | Waxman et al. | |
| 2019/0170900 | A1 * | 6/2019 | Rieker | G01M 3/202 |
| 2019/0195725 | A1 | 6/2019 | Waxman et al. | |
| 2019/0277753 | A1 | 9/2019 | Waxman et al. | |

FOREIGN PATENT DOCUMENTS

| | | |
|---|---|---|
| CN | 103503135 A | 1/2014 |
| WO | WO-02/27297 A1 | 4/2002 |
| WO | WO-2017/201194 A1 | 11/2017 |
| WO | WO-2018/170438 A1 | 9/2018 |
| WO | WO-2019/099096 A1 | 5/2019 |
| WO | WO-2020/154619 A2 | 7/2020 |

OTHER PUBLICATIONS

Buchwitz, M. et al., Atmosphere methane and carbon dioxide from SCIAMACHY satellite data, Atmos. Chem. Phys., 5:941-962 (2005).
Byer, R. L. And Shepp, L. A., Two-dimensional remote air-pollution monitoring via tomography, Optics Letters, 4(3):75-77 (1979).
Clark, R. N. et al., Reflectance spectroscopy of organic compounds: Alkanes, J. Geophysical Research, 114:E030001:1-19, (2009).
Epperson, D. et al., Equivalent Leak Definitions for Smart LDAR (Leak Detection and Repair) When Using Optical Imaging Technology, Journal of the Air & Waste Management Association, 57(9):1050-1060, (2007).
Furry, D. et al., Detection of Volatile Organic Compounds (VOC's) with a Spectrally Filtered Cooled Mid-Wave Infrared Camera, Inframation Proceedings, Document No. ITC 108A Jun. 1, 2005, 6 pages, (2005).
Gottwald, M. et al., The Instrument, Chapter 3 in SCHIAMACHY—Exploring the Changing Earth's Atmosphere, pp. 29-46, (2006).
Gross, W. et al., Localization of Methane Distributions by Spectrally Tuned Infrared Imaging, SPIE, Part of the SPIE Conference on Air Monitoring and Detection of Chemical and Biological Agents, 3533:234-240, (1998).
Inada, H. et al., Uncooled SWIR InGaAs/GaAsSb type II quantum wells focal plane array, Proc. of SPIE, Infrared Technology and Applications XXXVI, 7660:76603N-1-76603N-7 (2010).
Shulz, M. et al., High-resolution thermophysical measurements using staring infrared detector arrays, High Temperatures—High Pressures, 32:547-556 (2000).
Van Den Bosch, C. J. H. and Duijm, N. J., Overflow and Spray release, Chapter 2, Methods for Calculation of Physical Effects: Due to Release of Hazardous Materials (Liquids & Gases)., EDS: Van den Bosch et al., 3rd Ed. 2nd Printing, CPR 14E, TNO—The Netherlands Organization of Applied Scientific Research, pp. 2.1-2.179 (2005).
Zhaoci, L. et al., LNG continuous leakage and diffusion process simulation, CIESC Journal, 66(S2):158-165, (2015).
International Search Report for PCT/US2020/014990, filed Jan. 24, 2020, 7 pages, (dated Aug. 24, 2020).
Written Opinion for PCT/US2020/014990, filed Jan. 24, 2020, 15 pages, (dated Aug. 24, 2020).

* cited by examiner

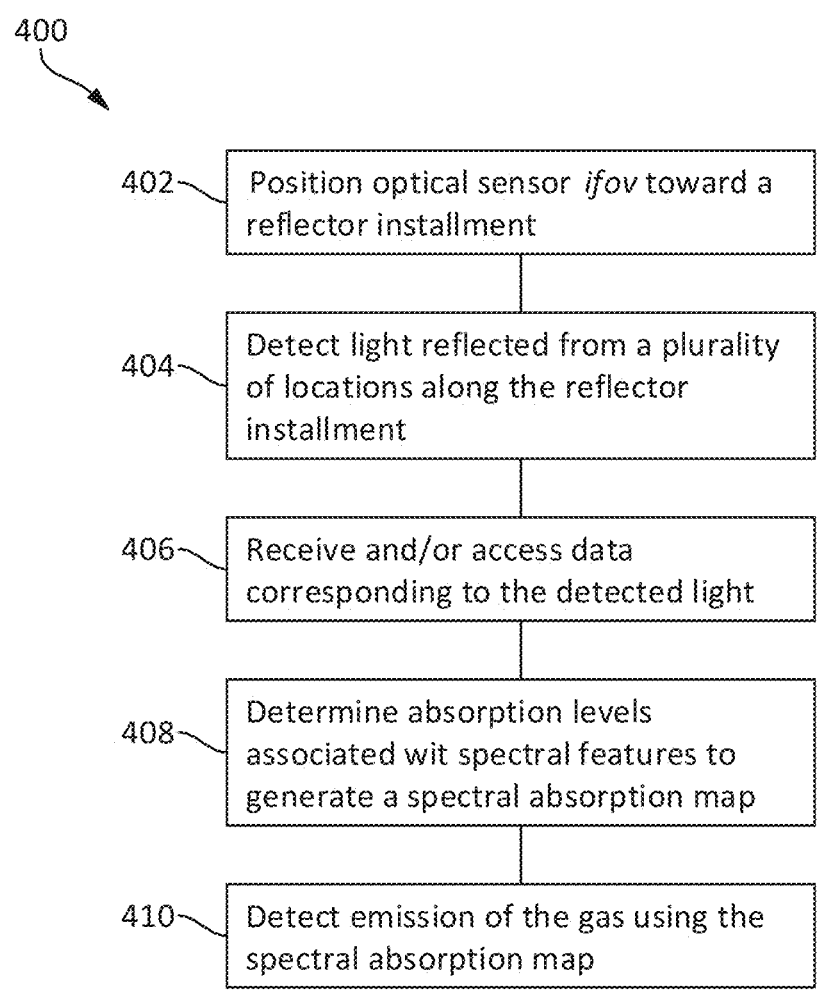

SYSTEMS AND METHODS FOR LEAK MONITORING VIA MEASUREMENT OF OPTICAL ABSORPTION USING TAILORED REFLECTOR INSTALLMENTS

CROSS-REFERENCE TO RELATED APPLICATIONS

This application claims priority to and benefit of U.S. Provisional Patent Application No. 62/797,065, entitled "Systems and Methods for Leak Monitoring via Measurement of Optical Absorption Using Tailored Reflector Installments" and filed Jan. 25, 2019, the content of which is hereby incorporated by reference herein in its entirety.

FIELD OF THE INVENTION

This invention relates generally to methods, systems, and apparatus for detection of emission of gas, e.g., methane, other hydrocarbons, carbon dioxide or ammonia, via measurement of optical absorption and tailored reflector installments. In particular, in certain embodiments, this invention relates to methods, systems, and apparatus for detection, localization and quantification of emission of multiple gases from within a site to be monitored via a scanning illuminator co-located with an optical sensor in combination with the tailored reflector installment.

BACKGROUND OF THE INVENTION

Natural gas leaks create both safety and environmental hazards, and occur along the entire gas supply chain from the well to the street (so-called upstream, midstream, and downstream sectors). Methane, the primary constituent of natural gas, is combustible in air, and is also a potent greenhouse gas. Other hydrocarbons found in natural gas, as well as vapors emanating from liquids separated from gas and oil, include ethane, propane, butane, pentane, hexane, octane, ethylene and heavier hydrocarbons, which form volatile organic compounds that generate smog which is a health hazard. Thus, there are compelling reasons to detect leaks of gases comprising, for example, methane and other hydrocarbons, so that such leaks can be repaired. In addition, methane and carbon dioxide are of significance due to their forcing effects on climate change. Thus, detecting and quantifying these emissions are of environmental importance. Conventional point and line detectors for gases have limited spatial coverage for detection as they rely on wind or air movements to transport the gas towards the point or line detector. Such air currents can easily transport the gas away from point detectors and around the open sensing path of line detectors. For gas safety applications a high degree of asset coverage is desired, in order to maximize the degree of certainty that a gas leak from assets of interest is detected under all circumstances. Thus, a solution that increases the degree of detection coverage for assets in a given area is very desirable.

Beyond merely detecting the presence of leaking gas, localizing leaks to particular assets (or particular components) and quantifying the leak rate (e.g., emission flux of leaking gas) are important for allowing repair of leaks to be performed rapidly, and in a prioritized fashion. Quantification of leak rate also allows the impact (e.g., environmental impact) of leaking gas to be assessed. Detection, localization, and quantification of gas leaks is challenging, since leak monitoring and/or inspection typically need to be performed over wide areas, and from a safe and practical standoff distance.

Accordingly, there exists a need for improved systems and methods for detection, localization, and quantification of gas leaks. In particular, there is a need for systems and methods that allow for effective gas leak monitoring and/or inspection to be performed over wide areas in complex environments, and even in the presence of interfering background signals. Cost effective solutions are particularly important, as they can be broadly adopted and utilized.

SUMMARY OF THE INVENTION

Presented herein are systems and methods directed to a multispectral absorption-based imaging approach that provides for rapid and accurate detection, localization, and quantification of gas emission from within a site to be monitored. The imaging technology described herein utilizes an optical sensor and broadband illumination in combination with specialized reflector installments mounted about the site. The optical sensor detects light from (e.g., ambient sunlight and/or a beam of artificial illumination reflected from) a plurality of sampled locations along the reflector installment, for example by imaging multiple sampled locations at a time and/or scanning an instantaneous field of view (ifov) of the optical sensor. Lines-of-sight from the optical sensor to sampled locations along the reflector installment sweep out an "optical curtain" partially enclosing and/or forming a boundary near various assets to be monitored (e.g., well-pads, compressor coolers, fracking rigs, LNG engines, platforms, tankers, landfills, temporary work sites including repairs of underground pipelines, and the like). If a leak is present, emitted gas crosses the optical curtain resulting in optical absorption that can be used to detect the leak, localize, and even obtain quantitative measures characterizing it, such as an emanating mass flux.

Accordingly, by strategically positioning tailored reflector installments, assets can be monitored for emissions of gases such as hydrocarbons (e.g., methane) emanating from vents, hatches, pipes, and other leaking components. The technology may be applied to monitoring assets in the oil and gas industry, petrochemical industry, and LNG transfer operations to vessels and vehicles, in environments that are outdoors, indoors, on shore, and off shore. Accordingly, the approaches described herein have implications in both environmental and safety monitoring applications.

In particular, in certain embodiments, the systems and methods described herein detect light within one or more specific spectral bands of interest that are selected to overlap with spectral features of various compounds to be detected. As light travels to the sensor, it may be absorbed by intervening gas (e.g., produced by a leak). Absorption of light by gas produces spectral signatures that are indicative of and specific to various compounds (e.g., hydrocarbons) that are present in the gas. Accordingly, by detecting light absorption in a spectrally sensitive manner (e.g., using various spectral filters placed in front of one or more detectors) different gases and compounds present therein can be detected and identified. As the optical sensor is scanned along the reflector installment, a multispectral absorption map can be created and used to detect and quantify gas leaks.

In certain embodiments, spectral bands within the short-wave infrared (SWIR) region (e.g., from about 1.0 to 2.6 microns) are of particular interest. This wavelength range includes spectral features associated with a number of important hydrocarbon compounds, such as methane, ethane, propane, butane, pentane, hexane, octane, ethylene and other hydrocarbons, as well as carbon dioxide and ammonia, and also offers advantages such as reduced atmospheric water vapor absorption and the possibility of sensitive detection without needing to use specialized (e.g., liquid nitrogen cooled) detectors.

Moreover, by increasing the amount of light that is directed back, from either a dedicated illumination source or ambient light, including solar illumination, use of tailored reflector installments offers a flexible and relatively inexpensive way to significantly increase range on detection systems, e.g., without needing to dramatically increase a power of an illumination source. Imaging systems designed in accordance with the approaches described herein can, accordingly, be widely implemented for gas emission monitoring of various sites of interest. For example, in certain embodiments, a reflective material (e.g., glass bead or prismatic retroreflective tape, retroreflective paint, loose retro-reflector spheres or crystals, etc.) can be placed on and/or nearby various assets of interest, such as compressors, gas storage tanks, or vehicles. Tailored panels and/or frames can also be mounted on, or so as to partially surround, assets to be monitored. Such reflective panels can also be mounted onto relocatable structures, such as posts mounted on stands or wheeled platforms, such that they may be deployed temporarily at work sites. Thus, the approaches described herein can be utilized anywhere that can accommodate permanent or temporary installation of an optical sensor and the placement of a reflective material and/or sections on or near assets or areas to be monitored for gas emissions.

Accordingly, by providing imaging technologies capable of performing rapid and effective multi-spectral absorption-based imaging over wide areas and at distance, the systems and methods described herein overcome a number of challenges associated with previous systems and methods for detecting gas leaks and facilitate a variety of gas leak, emissions, and safety monitoring applications.

In one aspect, the invention is directed to a method of detecting emission of gas comprising one or more compounds of interest [e.g., hydrocarbon compounds (e.g., methane, ethane, propane, butane, pentane, hexane, octane, ethylene, and other hydrocarbons); e.g., other compounds such as carbon dioxide and ammonia], the method comprising: (a) positioning an instantaneous field of view (ifov) of an optical sensor toward a reflector installment mounted about a site to be monitored; (b) detecting (e.g., in a spectrally selective manner), with one or more detectors of the optical sensor, light within one or more spectral bands of interest [e.g., the one or more spectral bands of interest lying within the short-wave infrared (SWIR) spectrum (e.g., ranging from about 1.0 to 2.6 microns); e.g., the one or more spectral bands of interest lying within the visible through near-infrared spectrum (e.g., ranging from about 0.4 to 1.0 microns)], the detected light having been reflected from a plurality of sampled locations on the reflector installment [e.g., at least a portion of the plurality of sampled locations spaced sufficiently close (e.g., no greater than 1 meter apart; e.g., no greater than 50 cm apart; e.g., no greater than 25 cm apart; e.g., no greater than 10 cm apart; e.g., no greater than 1 cm apart) so as to provide a spatial resolution (e.g., between neighboring lines-of-sight from sampled locations to the optical sensor) commensurate with (e.g., sufficiently fine to detect; e.g., smaller than) a characteristic size of the emission of the gas (e.g., of a typical cloud or plume)] and captured within the ifov of the optical sensor, wherein at least a portion of the one or more spectral bands of interest overlap with one or more spectral features associated with [e.g., spectral absorption due to (e.g., and indicative of presence of)] the one or more compounds of interest {e.g., thereby detecting light travelling along lines-of-sight from each sampled location to the optical sensor and/or an illumination source (e.g., co-located with the optical sensor), to form an optical curtain (e.g., a surface substantially confined to a 2D plane; e.g., a surface not confined to a 2D plane and varying in 3D space) at least partially enveloping, and/or forming at least a partial boundary of, at least a portion of the site, or creating a surface that divides a site into multiple sectors [e.g., such that the optical curtain partially encloses a volume (e.g., comprising one or more assets being monitored), and/or forms an at least partial boundary of a volume (e.g., comprising one or more assets being monitored), from within which the emission of the gas can be detected; e.g., whereby gas emitted from within the volume crosses the optical curtain (formed by the lines-of-sight from each sampled location to the optical sensor), e.g., whereby gas emitted from one sector crosses the optical curtain into the other sector, resulting in detectable absorption (e.g., within at least a portion of the one or more spectral bands of interest) of light reflected from locations along the reflector installment as the light travels back to the optical sensor]}; (c) receiving and/or accessing, by a processor of a computing device, data corresponding to the detected light reflected from the plurality of sampled locations (e.g., wherein the plurality of sampled locations along the reflector installment define a surface corresponding to a segment of the reflector installment); (d) determining, by the processor, for each of the plurality of sampled locations, an absorption level associated with (e.g., due to) at least one of the one or more spectral features using the detected light, thereby generating a spectral absorption map comprising a plurality of absorption levels, each associated with a particular sampled location and spectral feature; and (e) detecting [e.g., by the processor (e.g., automatically)] the emission of the gas from within the site to be monitored using the generated spectral absorption map.

In certain embodiments, the method comprises directing a beam of illumination from an illumination source (e.g., an illumination source co-located with the optical sensor) and toward the reflector installment; and scanning the beam of illumination across at least a portion of the reflector installment, thereby illuminating the plurality of sampled locations (e.g., wherein the beam of illumination illuminates one or more of the sampled locations at a time as it is scanned)(e.g., such that the detected light is light from the illumination source that is reflected back to the optical sensor by the reflector installment).

In certain embodiments, the method comprises scanning the beam of illumination in a continuous fashion across a portion of a target region comprising the reflector installment, thereby illuminating the plurality of sampled locations along the reflector installment as well as other locations within the target region, not necessarily on the reflector installment.

In certain embodiments, the illumination source is a broadband source, such that the beam of illumination has a spectral bandwidth spanning a plurality of spectral features of [e.g., spectral absorption due to (e.g., and indicative of presence of)] the one or more compounds of interest [e.g., wherein the beam of illumination has a spectral bandwidth of at least 200 nanometer (e.g., at least 500 nanometers)]. In certain embodiments, the illumination source is a broadband short-wave infrared (SWIR) source [e.g., having a bandwidth of approximately 500 nanometer or more in the SWIR region (e.g., ranging from about 1.0 microns to 2.6 microns)].

In certain embodiments, the method comprises scanning the ifov of the optical sensor across the portion of the reflector installment in a synchronized fashion with the beam of illumination (e.g., so as to maintain overlap between illuminated locations on the reflector installment and the ifov of the sensor) and detecting, within the one or more spectral bands of interest, with the one or more detectors, the light reflected from each of the sampled locations along the reflector installment as the ifov is scanned [e.g., wherein the ifov captures light reflected from one or more of the sampled locations at time as it is scanned (e.g., wherein the ifov captures light reflected from a single sampled location at a time; e.g., wherein the ifov captures light from a plurality of sampled locations at a time (e.g., the one or more detectors comprising a plurality of pixels for sampling a plurality of spatial locations at a time))].

In certain embodiments, the illumination source is co-located with (e.g., and mechanically coupled to) the optical sensor [e.g., both located in close proximity to each other; e.g., mounted together on a rotation stage or a pan-tilt stage)], and wherein the method comprises scanning the beam of illumination and the ifov in tandem.

In certain embodiments, the method comprises scanning the ifov of the optical sensor across the portion of the reflector installment and detecting, within the one or more spectral bands of interest, with the one or more detectors, light reflected from each of the sampled locations along the reflector installment as the ifov is scanned [e.g., wherein the ifov captures light reflected from one or more of the sampled locations at time as it is scanned (e.g., wherein the ifov captures light reflected from a single sampled location at a time; e.g., wherein the ifov captures light from a plurality of sampled locations at a time (e.g., the one or more detectors comprising a plurality of pixels for sampling a plurality of spatial locations at a time)); e.g., wherein ambient light (e.g., sunlight) is sufficient to generate detectable signal (e.g., and no dedicated illumination source is needed)].

In certain embodiments, step (b) comprises detecting light from a plurality of image locations within a target region, wherein the target region comprises the reflector installment (e.g., the reflector installment is positioned within the target region) and the image locations comprise the plurality of sampled locations on the reflector installment, as well as other locations within the target region, not necessarily on the reflector installment (e.g., by scanning the ifov of the optical sensor in a continuous fashion across a portion of the target region).

In certain embodiments, step (c) comprises receiving and/or accessing data corresponding to the detected light from the plurality of image locations within the target region; and step (d) comprises determining, for each of the plurality of image locations (e.g., the plurality of sampled locations along the reflector installment, as well as other locations, not necessarily on the reflector installment), an absorption level associated with (e.g., due to) at least one of the one or more spectral features using the detected light, such that the generated spectral absorption map comprises a plurality of absorption levels, each associated with a particular image location and spectral feature.

In certain embodiments, the reflector installment comprises one or more continuous reflective sections of sufficient size to span a plurality of the sampled locations [e.g., two or more of the sampled locations are on a same, continuous, reflective surface; e.g., each continuous reflective section is at least twice (e.g., at least five times; e.g., at least ten times; e.g., at least 20 times) as large as an individual ifov of each of the one or more detectors along at least one dimension].

In certain embodiments, the reflector installment comprises one or more continuous reflective sections each comprising a plurality of individual retro-reflective elements (e.g., the reflection sections are panels comprised over many tiny retro-reflectors that cover extended strips or areas, as opposed to discreet corner cube reflectors that occupy points not areas or strips).

In certain embodiments, the one or more detectors comprise an array detector comprising a plurality of pixels and aligned to image a spatial region comprising two or more of the sampled locations (e.g., a two-dimensional focal plane array detector aligned to image a two-dimensional spatial region; e.g., a two-dimensional focal plane array detector aligned to image a one-dimensional spatial region; e.g., a one-dimensional array detector).

In certain embodiments, the one or more detectors are aligned to image a single spatial location at a time (e.g., a point detector comprising a single pixel; e.g., an array detection (e.g., a quadrant detector) comprising a plurality of pixels aligned to detect light from a substantially same spatial location (e.g., each pixel detecting light from within a different spectral band of interest)].

In certain embodiments, the reflector installment comprises one or more reflective sections mounted in proximity to (e.g., behind with respect to a location of the optical sensor; e.g., at least partially encircling; e.g., encircling), and/or mounted on, one or more assets [(e.g., one or more well pads; e.g., one or more compressor coolers; e.g., one or more fracking rigs; one or more liquid natural gas engines (e.g., of a ship); e.g., one or more floating liquid natural gas platforms; e.g., one or more liquid natural gas tankers; e.g., liquid natural gas loading/unloading equipment)] within the site (e.g., wherein the site is an interior site; e.g., wherein the site is an off-shore site; e.g., wherein the site is a liquid natural gas loading site; e.g., wherein the site is a temporary repair operations site; e.g., wherein the site is a plant undergoing commissioning and/or turnaround).

In certain embodiments, the reflector installment comprises one or more reflective sections, each comprising a reflective surface [e.g., the reflective surface having a reflectivity of greater than or equal to 50% (e.g., greater than or equal to 80%) across one or more spectral bands of interest] [e.g., a retroreflective surface (e.g., glass bead or prismatic retroreflective panels, retroreflective tape, a surface painted with retroreflective paint, a surface comprising retroreflective crystals (e.g., a surface to which loose retroreflective spheres or crystals are attached), etc.) (e.g., having a retro-reflective gain of greater than or equal to 10 (e.g., with respect to a diffuse reflector) across one or more spectral bands of interest)].

In certain embodiments, the reflector installment comprises one or more retro-reflective surfaces [e.g., glass bead or prismatic retroreflective panels, retroreflective tape, a surface painted with retroreflective paint, a surface comprising retroreflective crystals (e.g., a surface to which loose retroreflective spheres or crystals are attached), etc.; e.g., having a retro-reflective gain of greater than or approximately equal to 10 (e.g., with respect to a diffuse reflector) (e.g., greater than or approximately equal to 100)].

In certain embodiments, the optical sensor is positioned within 100 meters of a furthest portion of the reflector installment (e.g., within 50 meters of the furthest portion of the reflector installment; e.g., within 25 meters of the furthest portion of the reflector installment).

In certain embodiments, for each of one or more of the sampled locations along the reflector installment, an angle of incidence and/or exitence from a line of sight from the optical sensor to the sampled location along the reflector installment (e.g., the angle measured between a surface normal and the line of sight) is greater than 1 degree (e.g., greater than 5 degrees; e.g., greater than 10 degrees; e.g., greater than 20 degrees).

In certain embodiments, the reflector installment comprises one or more reflective surfaces, each having a minimum dimension sufficiently large to span, for each of the one or more detectors of the optical sensor, a projection of an individual ifov of the detector onto the reflective surface (e.g., such that an angle subtended by the minimum dimension of the reflective surface from a location of the optical sensor is greater than or approximately equal to the angular extent of the ifov).

In certain embodiments, the method comprises oversampling of the sensor ifov along at least one dimension (e.g., the minimum dimension) of each of the one or more reflective surfaces [e.g., to ensure that the projection of the individual ifov of each detector falls entirely on each reflective surface while scanning the sensor ifov over the reflective surfaces (e.g., wherein the minimum dimension of each reflective surface is comparable to the spot size of projection of the detector ifov at a maximum design operating range)].

In certain embodiments, the reflector installment comprises one or more approximately planar reflective surfaces (e.g., retro-reflective surfaces)[e.g., wherein the approximately planar surfaces are oriented approximately vertically or horizontally (e.g., and/or substantially perpendicular to a plane passing through the optical sensor and above the site to be monitored (e.g., such that the planar reflective surfaces are not tilted extremely up or down, towards the sky or ground))(e.g., one or more vertical and/or horizontal strip retro-reflectors)(e.g., each spanning an edge of one or more compressor coolers)].

In certain embodiments, the reflector installment comprises a frame comprising (e.g., covered with) a reflective surface (e.g., a retro-reflective surface) [e.g., the frame mounted behind and encircling a boundary of a site to be monitored (e.g., enclosing at least a portion of one or more tanks to be monitored); e.g., wherein the optical sensor is positioned within the site and the frame encircles the site (e.g., to provide for 360 degree coverage)][e.g., said frame consisting of approximately vertical posts and horizontal crossbars to which retro-reflective surfaces (e.g., retro-reflective panels and/or tapes) are affixed].

In certain embodiments, the reflector installment comprises one or more reflective surfaces (e.g., retro-reflective surfaces) (e.g., curved surfaces) each mounted along at least a portion of an edge of a tank to be monitored (e.g., a plurality of reflective surfaces, each reflective surface mounted along at least a portion of an edge of a tank and/or group of tanks to be monitored).

In certain embodiments, the reflector installment comprises one or more reflective surfaces (e.g., retro-reflective surfaces) mounted along walls of an interior site to be monitored (e.g., under a ceiling, e.g., to monitor gas accumulation).

In certain embodiments, at least a portion of the reflector installment is relocatable.

In certain embodiments, the method comprises performing steps (a) through (e) using two or more optical sensors [e.g., differently located optical sensors, positioned such that their lines-of-sight intersect; e.g., such that each optical sensor detects light from a different direction (e.g., 30 degrees or greater apart; e.g., 60 degrees or more apart; e.g., nearly 90 degrees apart)(e.g., to allow for tomographic sensing to intersect lines of integrated column density in order to localize the emission of the gas)](e.g., scanning the ifov of each optical sensor over a corresponding portion of the reflector installment)(e.g., to generate two spectral absorption maps, e.g., and using the two spectral absorption maps to localize a location of the emission; e.g., via tomographic sensing).

In certain embodiments, the optical sensor is rotatable [e.g., wherein the method comprises performing steps (a) through (f) to scan a first portion of the reflector installment and monitor a first portion of the site, then rotating the optical sensor and performing steps (a) through (f) to scan a second portion of the reflector installment to monitor a second portion of the site].

In certain embodiments, the one or more detectors comprise one or more spectral detectors, each associated with a particular spectral band of the one or more spectral bands of interest and operable to distinguishably detect (e.g., by virtue of a spectral filter that is transmissive to wavelengths within the particular spectral band and positioned in front of the active area of the detector) light within the particular spectral band.

In certain embodiments, the one or more spectral bands of interest are within the short-wave infrared (SWIR) spectrum (e.g., ranging from about 1.0 to 2.6 microns).

In certain embodiments, each of at least a portion of the one or more spectral bands of interest span an extended spectral feature, comprising a plurality of absorption lines of the one or more compounds of interest [e.g., the portion of the one or more spectral bands of interest having a spectral bandwidth of about 50 nanometers or more, e.g., about 100 nanometers or more; e.g., about 200 nanometers or more].

In certain embodiments, the method further comprises using the data corresponding to the detected light to quantify the emission of the gas from within the site [e.g., using the data (e.g., to determine a measure of column density of the gas) in combination with a measure of wind speed and direction (e.g., crossing the optical curtain) and/or a buoyancy of the gas; e.g., to determine at least one of a total volume of the emission of the gas, a total mass of the emission of the gas, a mass flux of the emission of the gas].

In certain embodiments, the method comprises using the data corresponding to the detected light to quantify a mass flux of the emission of the gas from within the site (e.g., from within each of at least a portion of one or more assets within the site).

In certain embodiments, the method comprises using the data corresponding to the detected light to quantify a mass flux of gas passing between a first sector and a second, neighboring (e.g., sharing a boundary with the first sector), sector (e.g., two sub-divisions, e.g., a hazardous sector and a non-hazardous sector) of the site [e.g., wherein lines of site from at least a portion of the sampled locations, to the optical sensor form a surface that sub-divides the site into the first and second sector, and or more sectors].

In another aspect, the invention is directed to a system for detecting emission of gas comprising one or more compounds of interest [e.g., hydrocarbon compounds (e.g., methane, ethane, propane, butane, pentane, hexane, octane, ethylene, and other hydrocarbons); e.g., other compounds such as carbon dioxide and ammonia], the system comprising: (a) a reflector installment mounted about a site to be monitored; (b) an optical sensor positioned in proximity to the reflector installment (e.g., within 100 meters of a furthest portion of the reflector installment; e.g., within 50 meters of a furthest portion of the reflector installment; e.g., within 25 meters of a furthest portion of the reflector installment) comprising one or more detectors, wherein: the one or more detectors are aligned and operable to detect light within one or more spectral bands of interest [e.g., wherein the one or more spectral bands of interest are within the short-wave infrared (SWIR) spectrum (e.g., ranging from about 1.0 to 2.6 microns); e.g., the one or more spectral bands of interest lying within the visible through near-infrared spectrum (e.g., ranging from about 0.4 to 1.0 microns)], at least a portion of said spectral bands of interest overlapping with one or more spectral features [e.g., spectral absorption due to (e.g., and indicative of presence of)] associated with the one or more compounds of interest, and the one or more detectors are aligned to detect light reflected from a plurality of sampled locations on the reflector installment [e.g., at least a portion of the plurality of sampled locations spaced sufficiently close (e.g., no greater than 1 meter apart; e.g., no greater than 50 cm apart; e.g., no greater than 25 cm apart; e.g., no greater than 10 cm apart; e.g., no greater than 1 cm apart) so as to provide a spatial resolution (e.g., between neighboring lines-of-sight from sampled locations to the optical sensor) commensurate with (e.g., sufficiently fine to detect; e.g., smaller than) a characteristic size of the emission of the gas (e.g., of a typical cloud or plume)] and captured within an instantaneous field of view (ifov) of the optical sensor {e.g., thereby detecting light travelling along lines-of-sight from each sampled location to the optical sensor and/or an illumination source (e.g., co-located with the optical sensor), to form an optical curtain (e.g., a surface substantially confined to a 2D plane; e.g., a surface not confined to a 2D plane and varying in 3D space) at least partially enveloping, and/or forming at least a partial boundary of, at least a portion of the site [e.g., such that the optical curtain partially encloses a volume (e.g., comprising one or more assets being monitored), and/or forms an at least partial boundary of a volume (e.g., comprising one or more assets being monitored), from within which the emission of the gas can be detected; e.g., whereby gas emitted from with the volume crosses optical curtain (formed by the lines-of-sight from each sampled location to the optical sensor), resulting in detectable absorption (e.g., within at least a portion of the one or more spectral bands of interest) of light reflected from locations along the reflector installment as the light travels to the optical sensor]}; (c) a processor of a computing device; and (d) a memory having instructions stored thereon, wherein the instructions, when executed by one processor, cause the processor to: receive and/or access, data corresponding to the detected light from each of the plurality of sampled locations (e.g., wherein the plurality of sampled locations along the reflector installment define surface corresponding to a surface of the reflector installment); determine, for each of the plurality of sampled locations, an absorption level associated with (e.g., due to) at least one of the one or more spectral features using the detected light, thereby generating a spectral absorption map comprising a plurality of absorption levels, each associated with a particular sampled location and spectral feature; and detect (e.g., automatically) the emission of the gas from with the site to be monitored using the generated spectral absorption map.

In certain embodiments, the system comprises a scanning illuminator aligned and operable to emit and direct a structured illumination beam (e.g., wherein the scanning illuminator is co-located with the optical sensor) towards the reflector installment and scan the structured illumination beam across at least a portion of the reflector installment, thereby illuminating the plurality of sampled locations (e.g., wherein the beam of illumination illuminates one or more of the sampled locations at a time as it is scanned)(e.g., such that the detected light is light from the illumination source that is reflected back to the optical sensor by the reflector installment).

In certain embodiments, the scanning illuminator is operable to scan the beam of illumination in a continuous fashion across a portion of a target region comprising the reflector installment, thereby illuminating the plurality of sampled locations along the reflector installment as well as other locations within the target region, not necessarily on the reflector installment.

In certain embodiments, the scanning illuminator is a broadband source, such that the beam of illumination has a spectral bandwidth spanning a plurality of spectral features of [e.g., spectral absorption due to (e.g., and indicative of presence of)] the one or more compounds of interest [e.g., wherein the beam of illumination has a spectral bandwidth of at least 200 nanometer (e.g., at least 500 nanometers)]. In certain embodiments, the scanning illuminator comprises a broadband short-wave infrared (SWIR) source [e.g., having a bandwidth of approximately 500 nanometer or more in the SWIR region (e.g., ranging from about 1.0 microns to 2.6 microns)].

In certain embodiments, the system comprises an optical sensor scanner operable to scan the ifov of the optical sensor across the portion of the reflector installment in a synchronized fashion with the beam of illumination (e.g., so as to maintain overlap between illuminated locations on the reflector installment and the ifov of the sensor) and so as to detect, with the one or more detectors, within the one or more spectral bands of interest, the light reflected from each of the sampled locations along the reflector installment as the ifov is scanned [e.g., wherein the ifov captures light reflected from one or more of the sampled locations at time as it is scanned (e.g., wherein the ifov captures light reflected from a single sampled location at a time; e.g., wherein the ifov captures light from a plurality of sampled locations at a time (e.g., the one or more detectors comprising a plurality of pixels for sampling a plurality of spatial locations at a time))].

In certain embodiments, the scanning illuminator is co-located with (e.g., and mechanically coupled to) the optical sensor [(e.g., both located in close proximity to each other; e.g., mounted together on a rotation stage or a pan-tilt stage)], such that both the beam of illumination and the ifov are scanned in tandem.

In certain embodiments, the system comprises an optical sensor scanner operable to scan the ifov of the optical sensor across at least a portion of the reflector installment, so as to detect, with the one or more detectors, within the one or more spectral bands of interest, light reflected from each of the sampled locations along the reflector installment as the ifov is scanned [e.g., wherein the ifov captures light reflected from one or more of the sampled locations at time as it is scanned (e.g., wherein the ifov captures light reflected from a single sampled location at a time; e.g., wherein the ifov captures light from a plurality of sampled locations at a time (e.g., the one or more detectors comprising a plurality of pixels for sampling a plurality of spatial locations at a time)) e.g., wherein ambient light (e.g., sunlight) is sufficient to generate detectable signal (e.g., and no dedicated illumination source is needed)].

In certain embodiments, the reflector installment comprises one or more continuous reflective sections of sufficient size to span a plurality of the sampled locations [e.g., two or more of the sampled locations are on a same, continuous, reflective surface; e.g., each continuous reflective section is at least twice (e.g., at least five times; e.g., at least ten times; e.g., at least 20 times) as large as an individual ifov of each of the one or more detectors along at least one dimension].

In certain embodiments, the reflector installment comprises one or more continuous reflective sections each comprising a plurality of individual retro-reflective elements (e.g., the reflection sections are panels comprised over many tiny retro-reflectors that cover extended strips or areas, as opposed to discreet corner cube reflectors that occupy points not areas or strips).

In certain embodiments, the one or more detectors comprise an array detector comprising a plurality of pixels and aligned to image a spatial region comprising two or more of the sampled locations (e.g., a two-dimensional focal plane array detector aligned to image a two-dimensional spatial region; e.g., a two-dimensional focal plane array detector aligned to image a one-dimensional spatial region; e.g., a one-dimensional array detector).

In certain embodiments, the one or more detectors are aligned to image a single spatial location at a time [e.g., a point detector comprising a single pixel; e.g., an array detection (e.g., a quadrant detector) comprising a plurality of pixels aligned to detect light from a substantially same spatial location (e.g., each pixel detecting light from within a different spectral band of interest)].

In certain embodiments, the reflector installment comprises one or more reflective sections mounted in proximity to (e.g., behind with respect to a location of the optical sensor; e.g., at least partially encircling; e.g., encircling), and/or mounted on, one or more assets [(e.g., one or more well pads; e.g., one or more compressor coolers; e.g., one or more fracking rigs; one or more liquid natural gas engines (e.g., of a ship); e.g., one or more floating liquid natural gas platforms; e.g., one or more liquid natural gas tankers; e.g., liquid natural gas loading/unloading equipment)] within the site (e.g., wherein the site is an interior site; e.g., wherein the site is an off-shore site; e.g., wherein the site is a liquid natural gas loading site; e.g., wherein the site is a temporary repair operations site; e.g., wherein the site is a plant undergoing commissioning and/or turnaround).

In certain embodiments, the reflector installment comprises one or more reflective sections, each comprising a reflective surface [e.g., the reflective surface having a reflectivity of greater than or equal to 50% (e.g., greater than or equal to 80%) across one or more spectral bands of interest] [e.g., a retroreflective surface (e.g., glass bead or prismatic retroreflective panels, retroreflective tape, a surface painted with retroreflective paint, a surface comprising retroreflective crystals (e.g., a surface to which loose retroreflective spheres or crystals are attached), etc.) (e.g., having a retroreflective gain of greater than or equal to 10 (e.g., with respect to a diffuse reflector) across one or more spectral bands of interest)].

In certain embodiments, the reflector installment comprises one or more retroreflective surfaces [e.g., glass bead or prismatic retroreflective panels, retroreflective tape, a surface painted with retroreflective paint, a surface comprising retroreflective crystals (e.g., a surface to which loose retroreflective spheres or crystals are attached), etc.; e.g., having a retroreflective gain of greater than or approximately equal to 10 (e.g., with respect to a diffuse reflector) (e.g., greater than or approximately equal to 100)].

In certain embodiments, the optical sensor is positioned within 100 meters of a furthest portion of the reflector installment (e.g., within 50 meters of the furthest portion of the reflector installment; e.g., within 25 meters of the furthest portion of the reflector installment).

In certain embodiments, for each of one or more of the sampled locations along the reflector installment, an angle of incidence and/or exitence from a line of sight from the optical sensor to the sampled location along the reflector installment (e.g., the angle measured between a surface normal and the line of sight) is greater than 1 degree (e.g., greater than 5 degrees; e.g., greater than 10 degrees; e.g., greater than 20 degrees).

In certain embodiments, the reflector installment comprises one or more reflective surfaces, each having a minimum dimension sufficiently large to span, for each of the one or more detectors of the optical sensor, a projection of an individual ifov of the detector onto the reflective surface (e.g., such that an angle subtended by the minimum dimension of the reflective surface from a location of the optical sensor is greater than or approximately equal to the angular extent of the ifov).

In certain embodiments, the system comprises an optical sensor scanner operable to scan the sensor ifov in a manner that over-samples along at least one dimension (e.g., the minimum dimension) of each of the one or more reflective surfaces [e.g., to ensure that the projection of the individual ifov of each detector falls entirely on each reflective surface while scanning the sensor ifov over the reflective surfaces (e.g., wherein the minimum dimension of each reflective surface is comparable to the spot size of projection of the detector ifov at a maximum design operating range)].

In certain embodiments, the reflector installment comprises one or more approximately planar reflective surfaces (e.g., retroreflective surfaces)[e.g., wherein the approximately planar surfaces are oriented approximately vertically or horizontally (e.g., and substantially perpendicular to a plane passing through the optical sensor and above the site to be monitored (e.g., such that the planar reflective surfaces are not tilted extremely up or down, towards the sky or ground))(e.g., one or more vertical and/or horizontal line retro-reflectors)(e.g., each spanning an edge of one or more compressor coolers)].

In certain embodiments, the reflector installment comprises a frame comprising (e.g., covered with) a reflective surface (e.g., a retroreflective surface) [e.g., mounted behind and encircling a boundary of a site to be monitored (e.g., enclosing at least a portion one or more tanks to be monitored); e.g., wherein the optical sensor is positioned within the site and the frame encircles the site (e.g., to provide for 360 degree coverage)][e.g., said frame consisting of approximately vertical posts and horizontal crossbars to which retroreflective surfaces (e.g., retroreflective panels and/or tapes) are affixed].

In certain embodiments, the reflector installment comprises one or more reflective surfaces (e.g., retroreflective surfaces) (e.g., curved surfaces) each mounted along at least a portion of an edge of a tank to be monitored (e.g., a plurality of reflective surfaces, each reflective surface mounted along at least a portion of an edge of a tank and/or group of tanks to be monitored).

In certain embodiments, the reflector installment comprises one or more reflective surfaces (e.g., retroreflective surfaces) mounted along walls of an interior site to be monitored (e.g., under a ceiling, e.g., to monitor gas accumulation).

In certain embodiments, at least a portion of the reflector installment is relocatable.

In certain embodiments, the system comprises two or more optical sensors [e.g., differently located optical sensors, positioned such that their lines of sight intersect; e.g., such that each optical sensor detects light from a different direction (e.g., 30 degrees or greater apart; e.g., 60 degrees or more apart; e.g., nearly 90 degrees apart)(e.g., to allow for tomographic sensing to intersect lines of integrated column density in order to localize the emission of the gas)], and two optical sensor scanners, each associated with one of the optical sensors and operable to scan the ifov of the associated optical sensor over a corresponding portion of the reflector installment (e.g., and wherein the instructions cause the processor to generate two spectral absorption maps, e.g., and use the two spectral absorption maps to localize a location of the emission; e.g., via tomographic sensing).

In certain embodiments, the optical sensor and optical sensor scanner are rotatable [e.g., mounted on a rotatable stage (e.g., so that they can scan a first portion of the reflector installment and monitor a first portion of the site, then be rotated to scan a second portion of the reflector installment to monitor a second portion of the site)].

In certain embodiments, the one or more detectors comprise one or more spectral detectors, each associated with a particular spectral band of the one or more spectral bands of interest and operable to distinguishably detect (e.g., by virtue of a spectral filter that is transmissive to wavelengths within the particular spectral band and positioned in front of the active area of the detector) light within the particular spectral band.

In certain embodiments, the one or more spectral bands of interest are within the short-wave infrared (SWIR) spectrum (e.g., ranging from about 1.0 to 2.6 microns).

In certain embodiments, each of at least a portion of the one or more spectral bands of interest span an extended spectral feature, comprising a plurality of absorption lines of the one or more compounds of interest [e.g., the portion of the one or more spectral bands of interest having a spectral bandwidth of about 50 nanometers or more, e.g., about 100 nanometers or more; e.g., about 200 nanometers or more].

In certain embodiments, the instructions cause the processor to use the data corresponding to the detected light to quantify the emission of the gas from within the site [e.g., to use the data e.g., to determine a measure of column density of the gas) in combination with a measure of wind speed (e.g., crossing the optical curtain) and/or a buoyancy of the gas; e.g., to determine at least one of a total volume of the emission of the gas, a total mass of the emission of the gas, a mass flux of the emission of the gas].

In certain embodiments, the instructions cause the processor to use the data corresponding to the detected light to quantify a mass flux of the emission of the gas from within the site (e.g., from within each of at least a portion of one or more assets within the site).

In certain embodiments, the instructions cause the processor to use the data corresponding to the detected light to quantify a mass flux of gas passing between a first sector and a second, neighboring (e.g., sharing a boundary with the first sector), sector (e.g., two sub-divisions, e.g., a hazardous sector and a non-hazardous sector) of the site [e.g., wherein lines of site from at least a portion of the sampled locations, to the optical sensor form a surface that sub-divides the site into the first and second sector, and or more sectors].

In another aspect, the invention is directed to a reflector installment comprising one or more retroreflective sections (e.g., one or more retro-reflector panels and/or surfaces covered in retroreflective material (e.g., tape)), each mounted along a portion of an edge of an asset (e.g., a tank comprising one or more hydrocarbon compounds) to be monitored for gas emission, wherein: each retroreflective section is oriented substantially in a vertical direction, extending upwards with respect to a top of the asset to which it is mounted (e.g., and behind the asset with respect to an observation location where an optical sensor is or may be positioned); and a surface of each retroreflective section that is oriented inwards from the edge of the asset has a retroreflective gain greater than about 10 (e.g., greater than about 20; e.g., greater than about 50; e.g., greater than about 100) (e.g., in comparison with respect to a diffuse reflector) across one or more spectral bands of interest (e.g., across wavelength ranging from 1.0 to 2.6 microns).

In certain embodiments, each retroreflective section extends along at least about 10% of a perimeter (e.g., along at least 20% of the perimeter; e.g., along at least 50% of the perimeter) of the asset (e.g., a top of a tank).

In another aspect, the invention is directed to a reflector installment comprising a frame comprising (e.g., covered with) a retroreflective surface having a retroreflective gain greater than about 10 (e.g., greater than about 20; e.g., greater than about 50; e.g., greater than about 100)(e.g., in comparison with respect to a diffuse reflector) across one or more spectral bands of interest (e.g., across wavelength ranging from 1.0 to 2.6 microns), wherein said frame is mounted behind and encircling a boundary of a site to be monitored [e.g., enclosing at least a portion one or more assets to be monitored; e.g., wherein the frame encircles an optical sensor is positioned within the site (e.g., to provide for 360 degree coverage)][e.g., said frame consisting of approximately vertical posts and horizontal crossbars to which retroreflective surfaces (e.g., retroreflective panels and/or tapes) are affixed].

In another aspect, the invention is directed to a reflector installment comprising one or more approximately planar retroreflective sections, wherein: each approximately planar retroreflective section is oriented approximately vertically or horizontally (e.g., and substantially perpendicular to a plane passing through the optical sensor and above the site to be monitored (e.g., such that the planar surfaces are not tilted extremely up or down, towards the sky or ground))(e.g., is a vertical or horizontal line retro-reflectors); each approximately planar retroreflective section spans an edge of one or more assets (e.g., one or more compressor coolers); and a surface of each approximately planar retroreflective section that is oriented inwards from an edge of the asset has a retroreflective gain greater than about 10 (e.g., greater than about 20; e.g., greater than about 50; e.g., greater than about 100) (e.g., in comparison with respect to a diffuse reflector) across one or more spectral bands of interest (e.g., across wavelength ranging from 1.0 to 2.6 microns).

Features of embodiments described with respect to one aspect of the invention may be applied with respect to another aspect of the invention.

BRIEF DESCRIPTIONS OF THE DRAWINGS

The patent or application file contains at least one drawing executed in color. Copies of this patent or patent application publication with color drawing(s) will be provided by the Office upon request and payment of the necessary fee.

The foregoing and other objects, aspects, features, and advantages of the present disclosure will become more apparent and better understood by referring to the following description taken in conjunction with the accompanying drawings, in which:

FIG. 4 is a block flow diagram showing a process for detecting gas leaks via the tailored reflector installment approaches described herein, according to an illustrative embodiment.

Figure 7A:
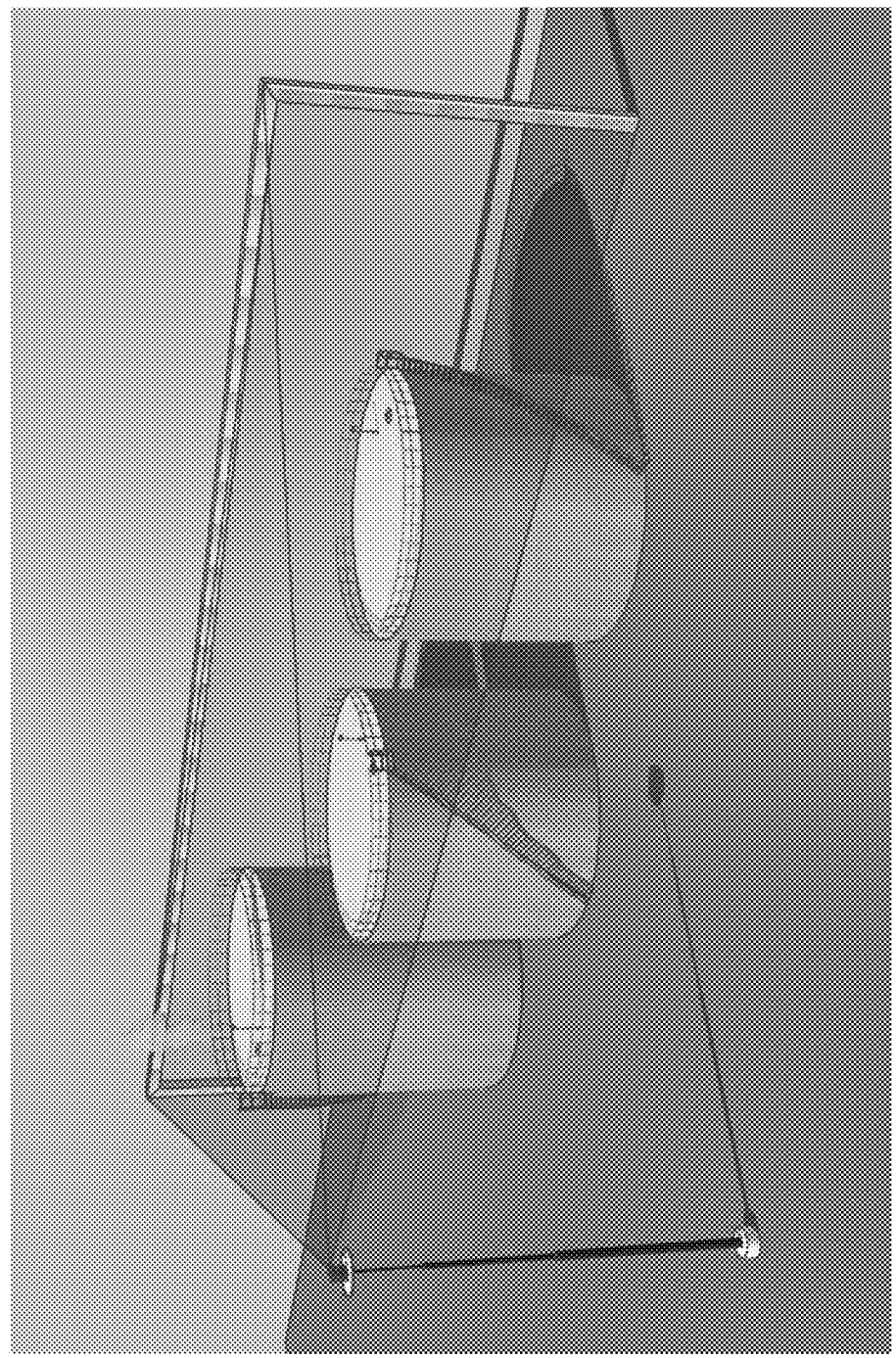

FIG. 7A is a schematic illustrating an optical curtain partially enclosing multiple tanks, according to an illustrative embodiment. The optical curtain is formed using a frame comprising retro-reflective posts and a crossbar, which form the top and sides of the curtain. A vertex of the optical curtain is at the scanning optical gas sensor and co-located illuminator. Vented gas may, for example, rise vertically through a top of the optical curtain.

Figure 7B:
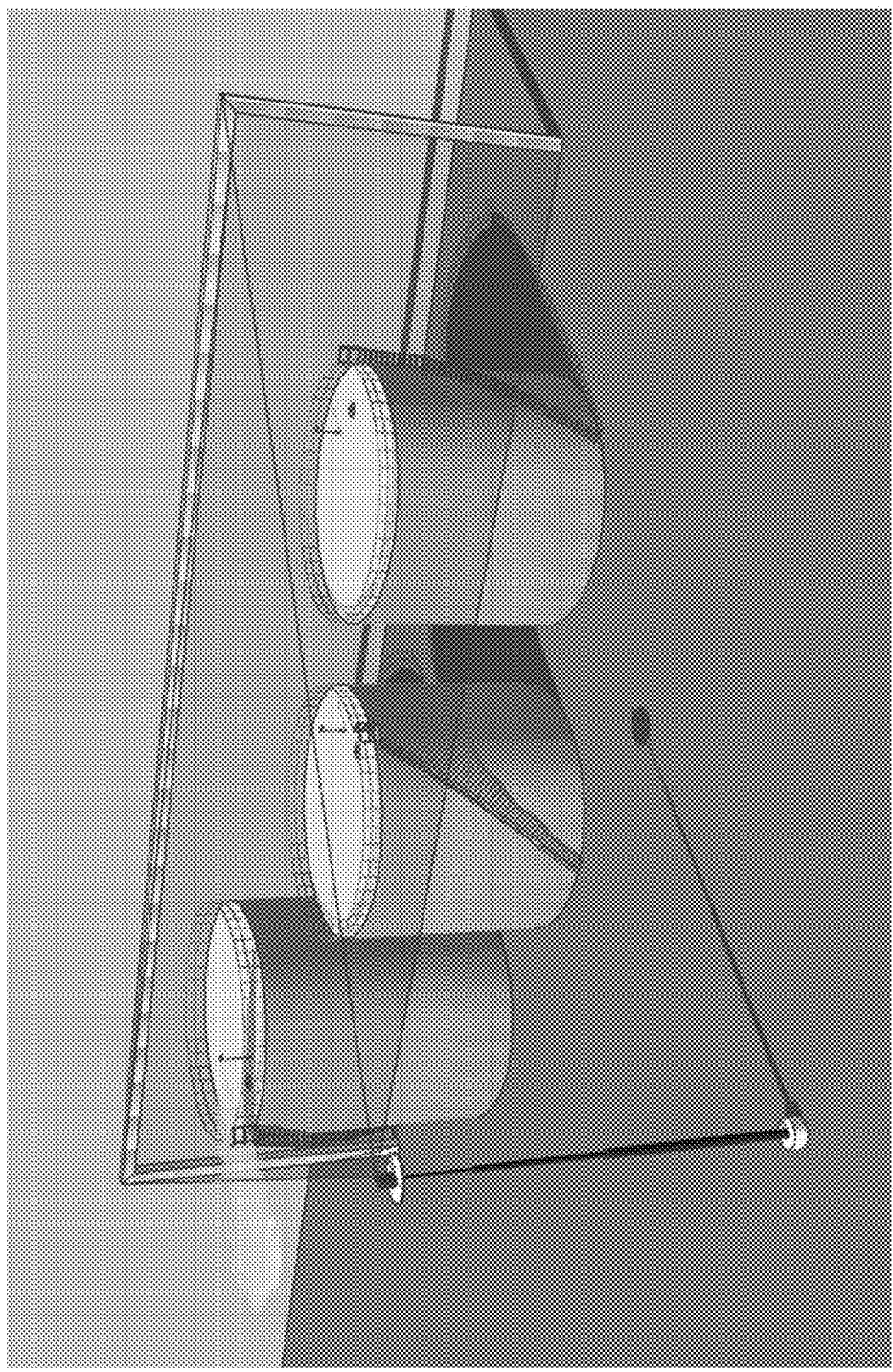

FIG. 7B is a schematic illustrating an optical curtain as in FIG. 7A, wherein vented gas disperses horizontally due to ambient winds, according to an illustrative embodiment.

Figure 8A:
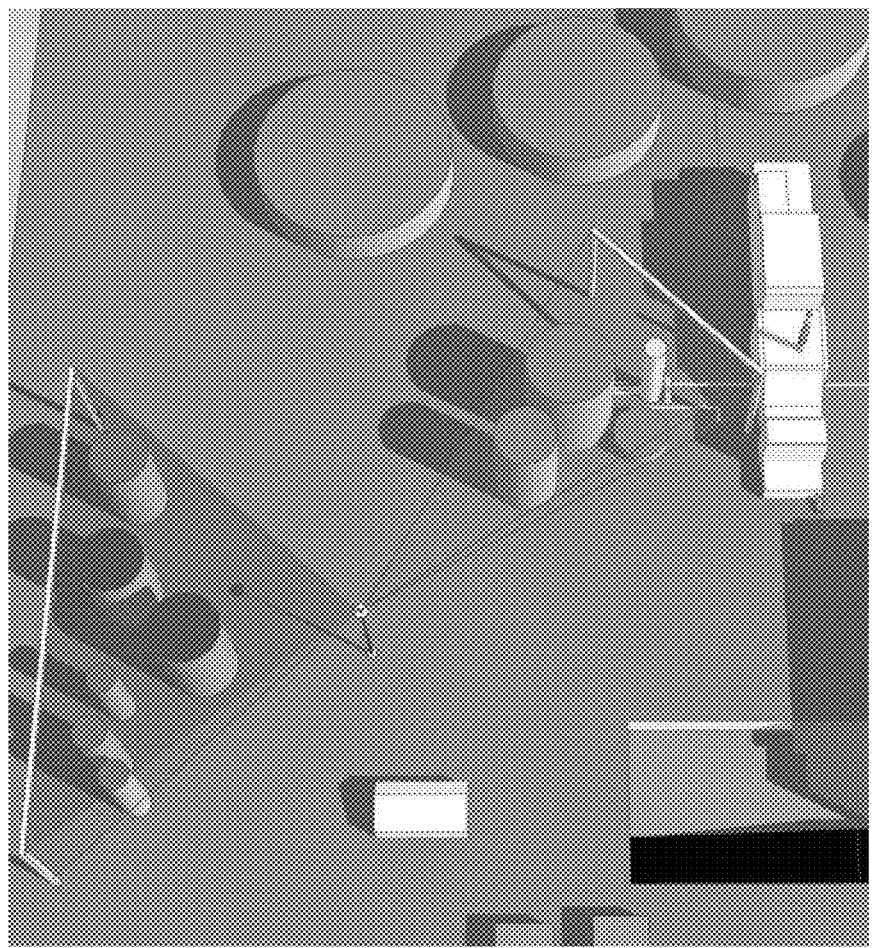

FIG. 8A is a schematic illustrating a top-down view of two monitored areas, each covered by optical curtains formed via a frame comprising retro-reflective posts and crossbars, along with a single scanning optical gas sensor and co-located illuminator, according to an illustrative embodiment.

Figure 8B:
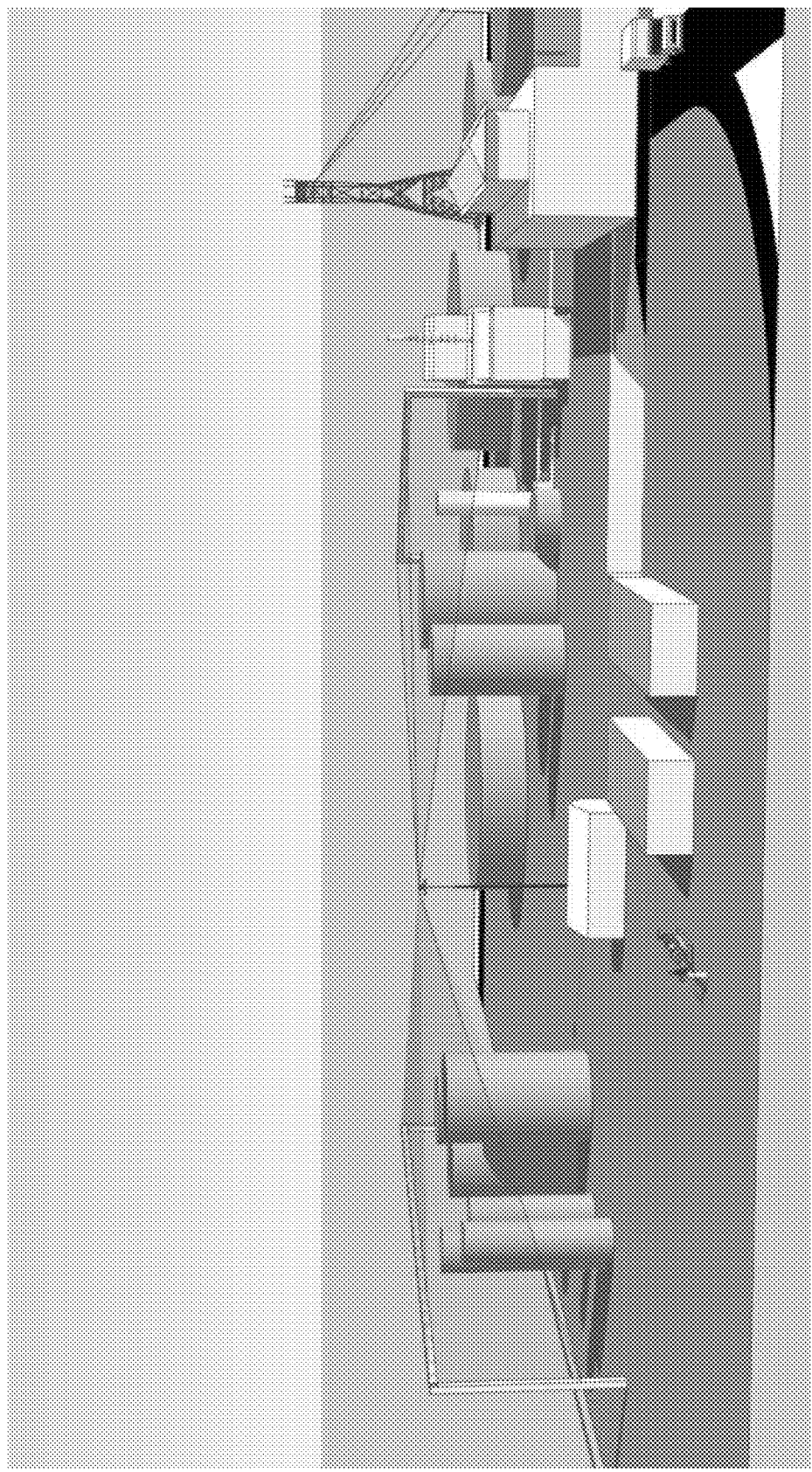

FIG. 8B is a schematic illustrating a side view of two monitored areas, each covered by optical curtains formed via a frame comprising retro-reflective posts and crossbars, along with a single scanning optical gas sensor and co-located illuminator, according to an illustrative embodiment.

Figure 9:
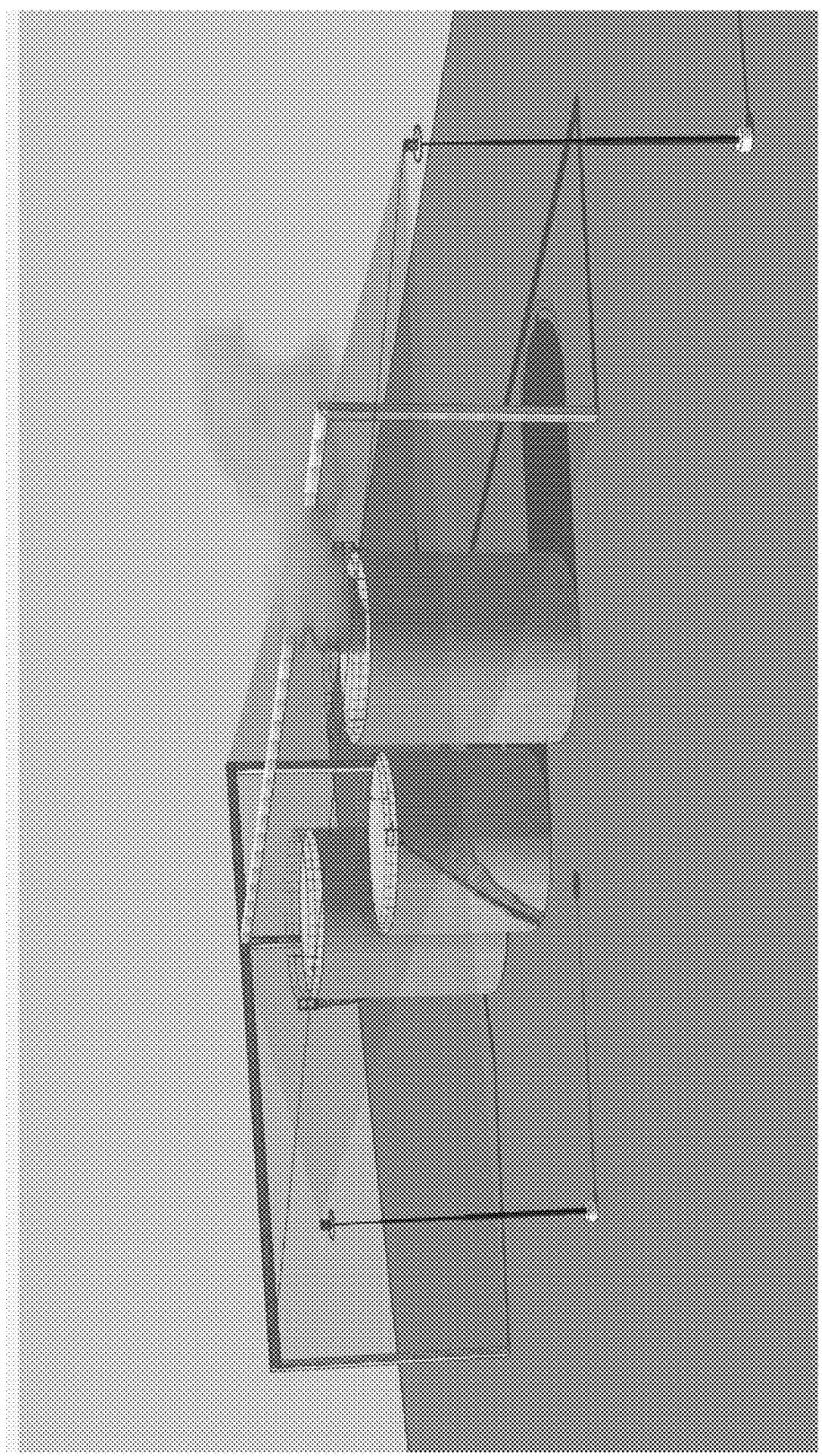

FIG. 9 is a schematic illustrating two optical sensors and co-located illuminators with two sets of retro-reflective posts and crossbars, each forming an optical curtain to enclose a group of multiple tanks to be monitored, according to an illustrative embodiment. The optical curtains cover a top and four sides about the group of tanks and allows for localization of leaks, as well as estimation of leak concentration and emission flux, in certain embodiments.

Figure 10A:
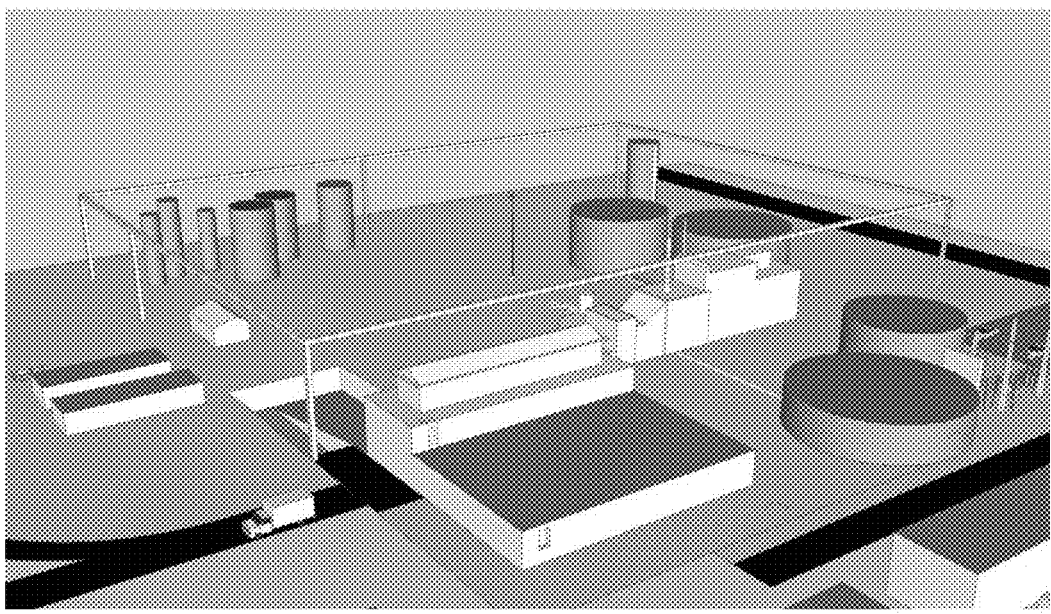

FIG. 10A is a schematic illustrating 360 degree coverage of assets by an optical curtain formed via a frame comprising retro-reflective posts and crossbars that surround an area, along with a single scanning optical gas sensor and co-located illuminator, according to an illustrative embodiment. In the embodiment shown in the figure, the scanning optical sensor and co-located illuminator are centrally mounted atop a tall mast.

Figure 10B:
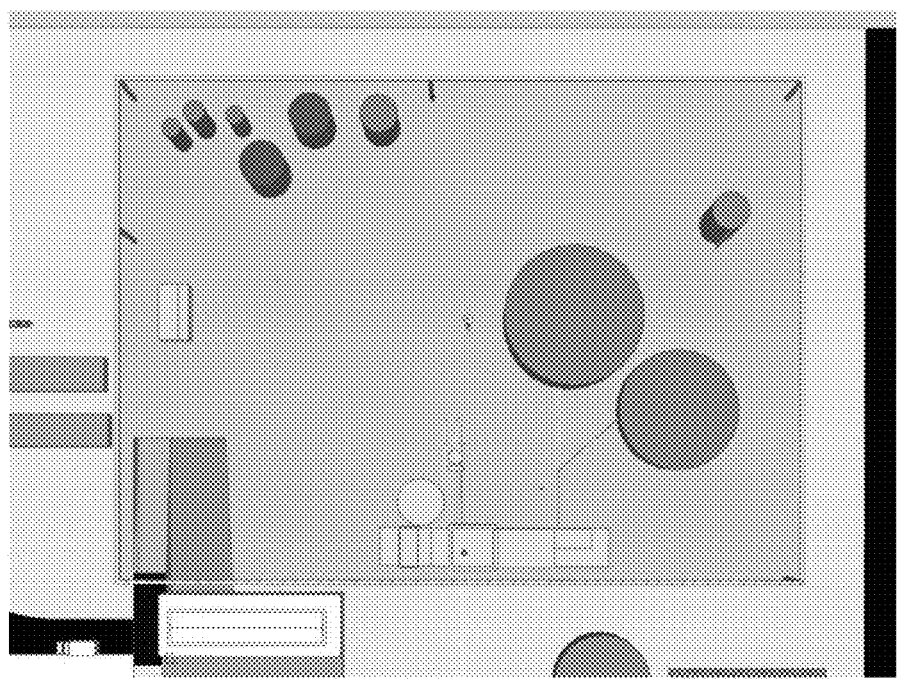

FIG. 10B is a schematic illustrating a top-down view of the embodiment shown in FIG. 10A.

Figure 11:
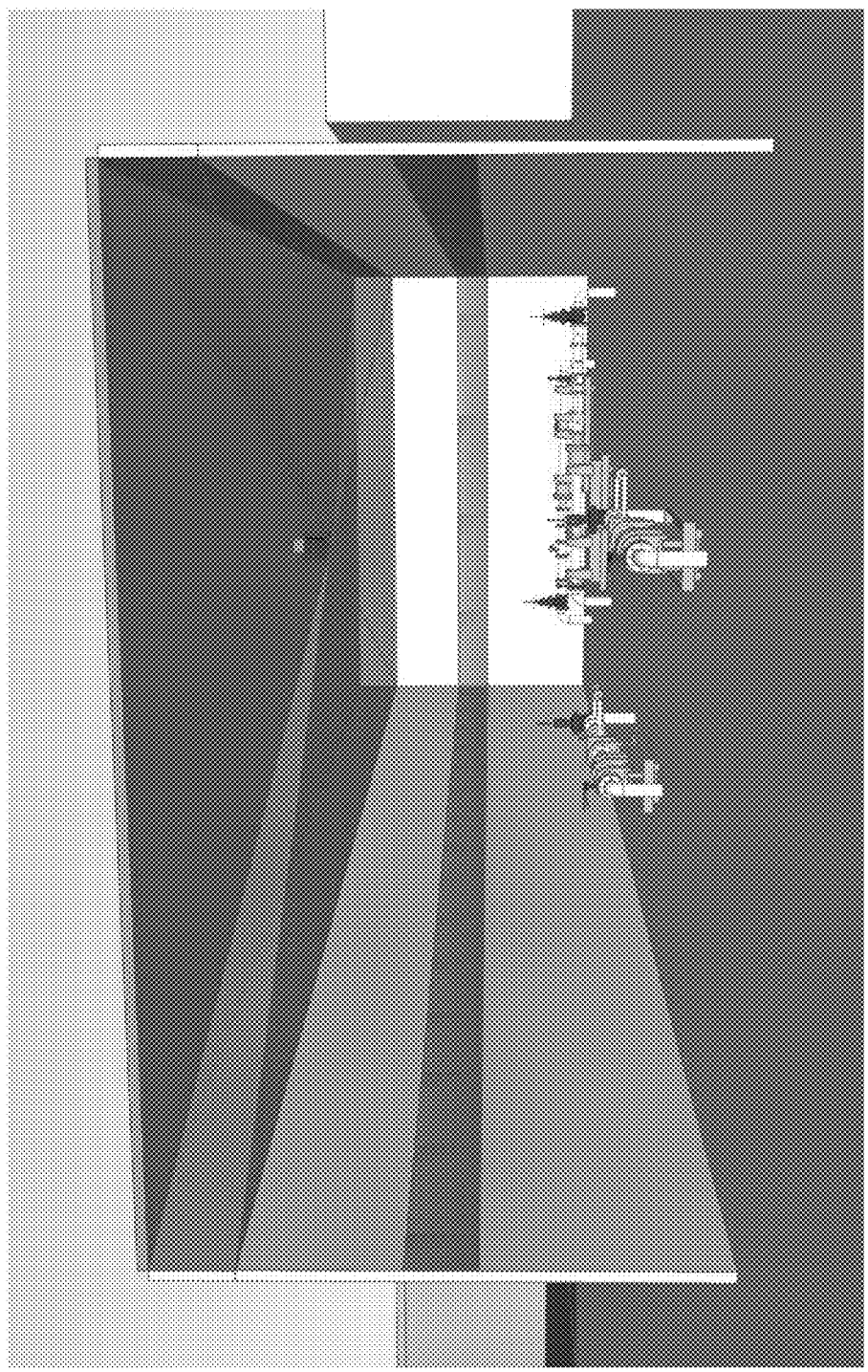

FIG. 11 is a schematic illustrating a system for monitoring for gas accumulating near a ceiling of an enclosed (or semi-enclosed) area using retro-reflective material mounted on interior walls along with a scanning optical gas sensor and co-located illuminator mounted to the ceiling, according to an illustrative embodiment.

Figure 12:

FIG. 12 is schematic showing an approach for monitoring LNG transfer onto a vessel using a retro-reflective blanket mounted around the a fueling portal of the vessel, and a nearby scanning optical gas sensor and co-located illuminator having line of sight to the fueling portal, according to an illustrative embodiment.

Figure 13:
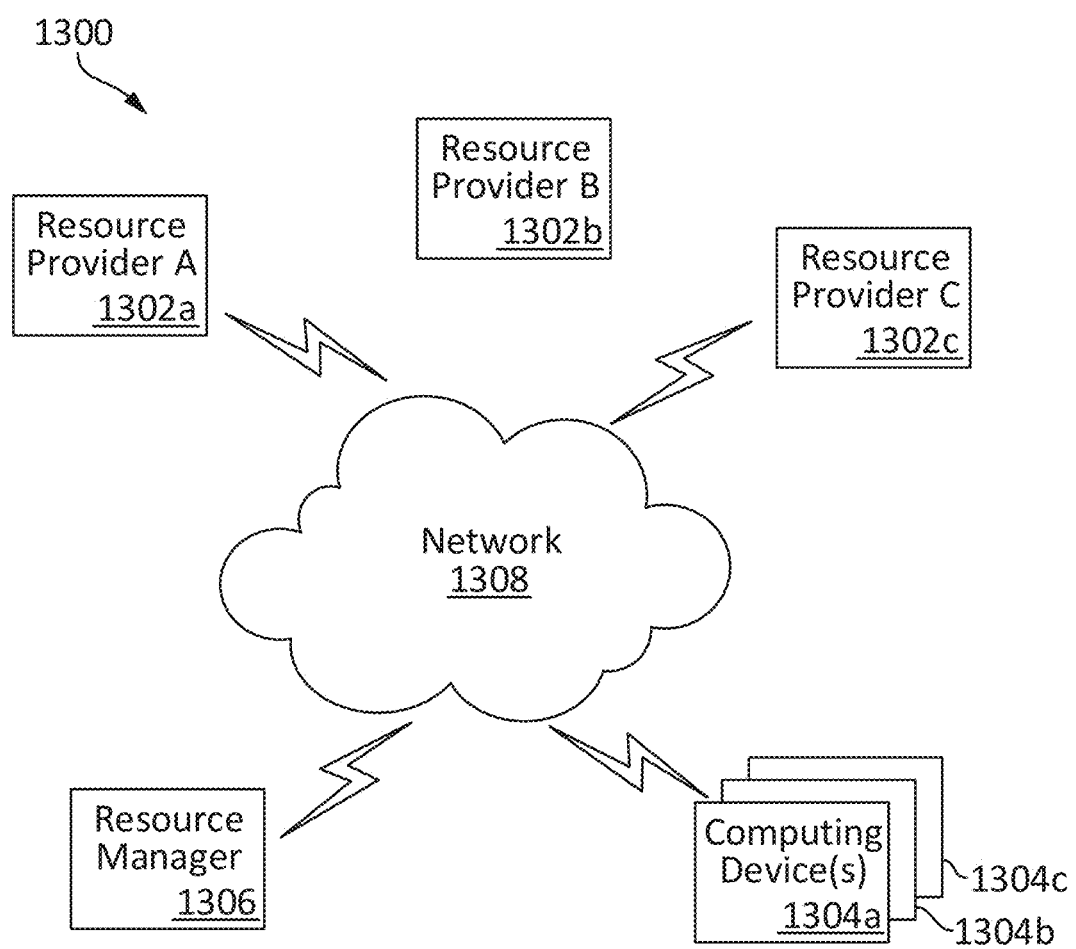
Figure 14:
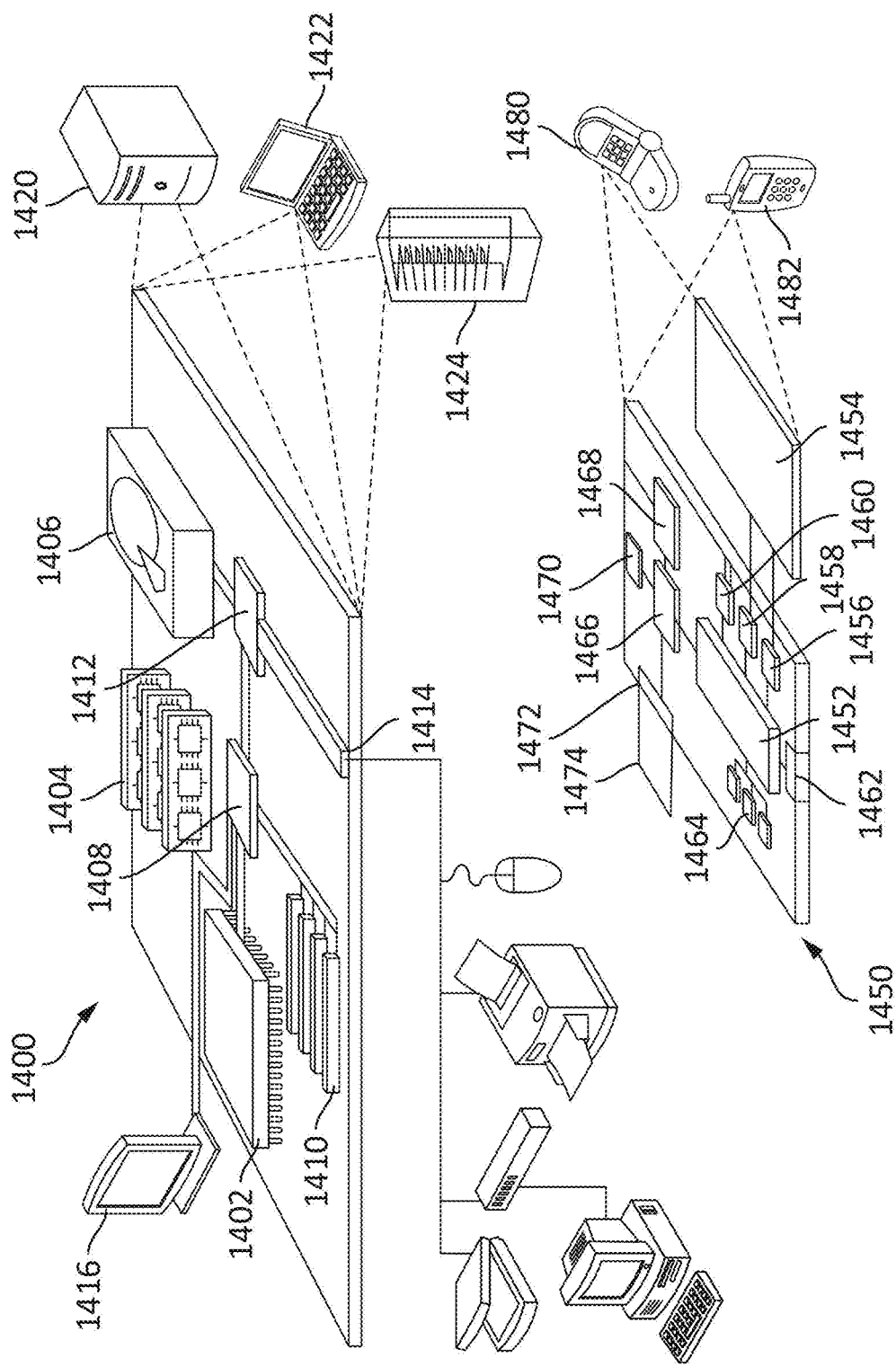

FIG. 13 is a block diagram of an exemplary cloud computing environment, used in certain embodiments FIG. 14 is a block diagram of an example computing device and an example mobile computing device used in certain embodiments.

Figure 15A:

FIG. 15A is a visible camera image with SWIR spectral imaging data overlaid demonstrating a three sided optical curtain for gas detection at a 5 meter distance.

Figure 15B:
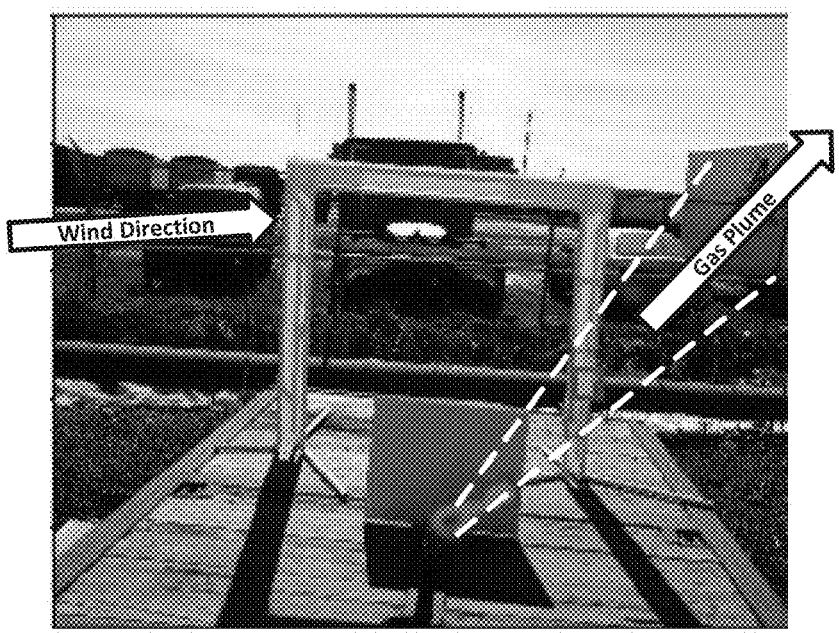

FIG. 15B is an annotated version of the image shown in FIG. 15A illustrating the interaction between wind and an emitted gas plume.

Figure 16:

FIG. 16 is a visible image with SWIR spectral imaging data overlaid demonstrating detection of gas emission at a 20 meter distance.

Figure 17:
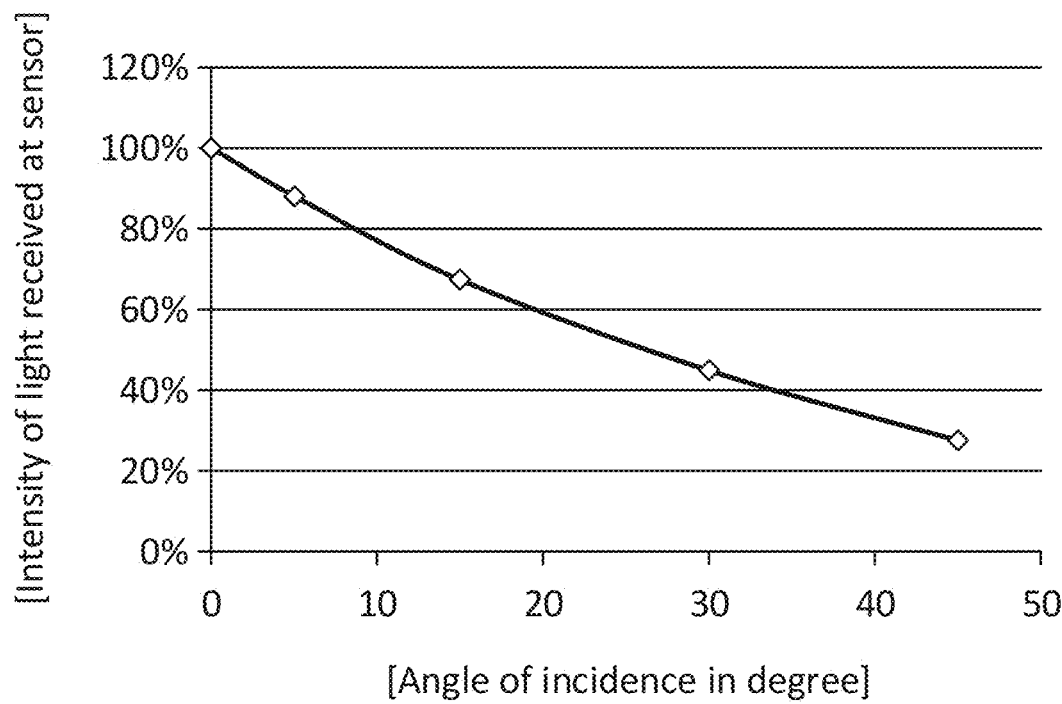

FIG. 17 is a graph showing angular dependence of light reflection from 3M Engineering Grade Prismatic (EGP) Reflective Sheeting 3430 in the 2250 nm-2350 nm band, measured from a 20 m distance.

Figure 18:
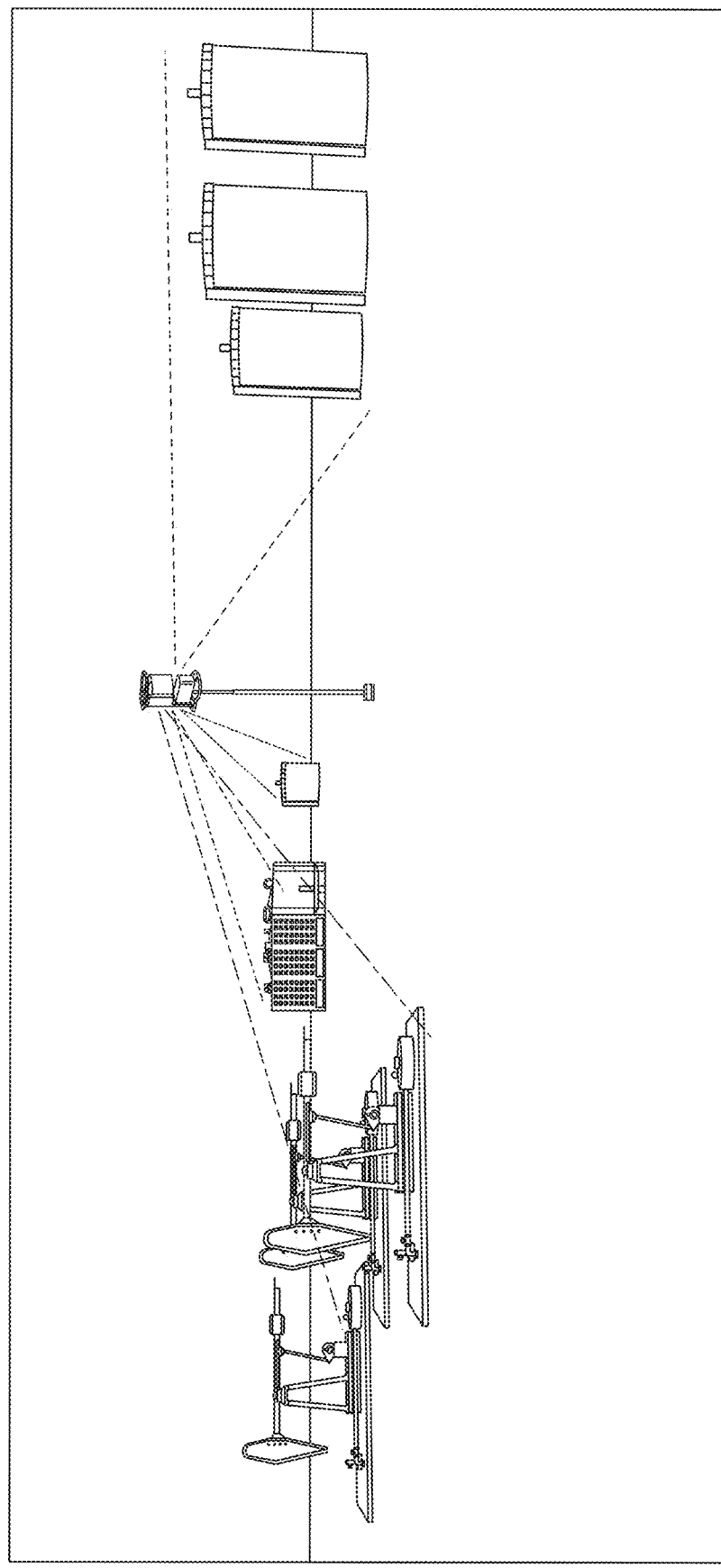

FIG. 18 is a schematic showing an optical sensor and co-located illuminator mounted on a lamppost and monitoring for gas leaks from four groups of assets located in separated areas across a site, according to an illustrative embodiment.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

Definitions

Asset: As used herein, the term "asset" refers to an object to be monitored for gas emission. In certain embodiments, assets refer to structures used for storage and/or transport of compounds of interest, such as various hydrocarbon compounds, including, but not limited to, methane, ethane, propane, butane, pentane, hexane, octane, heavier hydrocarbons or ethylene. Examples of assets include, without limitation, well pads, compressors and compressor coolers, storage or processing tanks, offshore installations, fracking rigs, liquid natural gas engines (e.g., of a ship), floating liquid natural gas platforms, liquid natural gas tankers, liquid natural gas loading/unloading equipment, above or underground pipelines, landfills, bitumen, or oilsand mines.

Reflector installment: As used herein, the term "reflector installment" refers to one or more sections of reflective material (e.g., retroreflective material) mounted within and/or about a site (e.g., comprising one or more assets or areas, such as temporary work sites, of interest) to be monitored for gas emission. The reflector installment may be permanently (e.g., adhered) or temporarily (e.g., a portable blanket or relocatable posts) affixed onto or placed nearby desired locations.

Mounted about: As used herein with reference to a reflector installment, the term "mounted about" refers to the permanent or temporary placing or installation of objects or material with, around, or on a new structure, a pre-existing structure, or a vehicle.

Spectral feature: As used herein, the term "spectral feature" refers to a group of one or more absorption lines associated with a particular compound of interest. In certain embodiments, a spectral feature comprises multiple (e.g., a plurality) of nearby absorption lines of the particular compound of interest (e.g., the spectral feature is an extended, or broadband spectral feature). In certain embodiments, such multiple nearby absorption lines are broad and overlap, producing a spectral feature comprising multiple partially overlapping absorption peaks. In certain embodiments, a bandwidth (e.g., full-width half maximum) of a spectral feature is about 50 nanometer or more. In certain embodiments, a bandwidth (e.g., full-width half maximum) of a spectral feature is about 100 nanometer or more.

DETAILED DESCRIPTION

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and apparatus are described as having, including, or comprising specific components, or where processes and methods are described as having, including, or comprising specific steps, it is contemplated that, additionally, there are articles, devices, systems, and apparatus of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Documents are incorporated herein by reference as noted.

Headers are provided for the convenience of the reader—the presence and/or placement of a header is not intended to limit the scope of the subject matter described herein.

The ability to continuously monitor large sized assets for methane emissions remains a significant challenge in the oil and gas, utility, petrochemical, and heavy industries. Natural gas compressors often leak methane from worn compressor seals. Oil well batteries and tank farms store crude oil that contains various hydrocarbon liquids and methane gas, and the methane can separate from the liquids venting out at the top of the tank. Some oil wells also release significant amounts of methane via casing vent gas at intermittent and unpredictable times. LNG loading operations leak methane. Repair operations of underground pipelines, including the pinpointing of leak sites, lead to venting of natural gas that creates safety concerns. Valves and flanges in refineries and petrochemical plants develop leaks of methane, ethane, VOCs, ethylene, other hydrocarbon gases, or liquid vapors. The presence of wind in outdoor environments limits the effectiveness of conventional point and line detectors for gases. Buoyant gases such as methane can form explosive atmospheres under ceilings inside buildings that are difficult to detect. Measurements are often collected in a highly localized fashion only and in units of concentration such as for example ppm (as opposed to a unit of emission flux of gas such as for example g/min) and do not allow conclusions about the size of a leak (e.g., the severity of the leak) and what priority a reaction to a leak should be given. Accordingly, there is a need to provide a cost effective solution to monitoring these and other asset types in order to detect and localize emission of methane and other gases or hydrocarbon liquid vapors, and to quantify the resulting emission flux. Commercially available gas detection solutions exist in the form of point sampling gas "sniffers", open path infrared (IR) line sensors, and thermal IR gas cameras. Point samplers cannot provide wide area coverage and do not respond until gas migrates from the leak site to the location of the sampler. Open path IR line sensors provide a means to detect gas passing through the single line of sight between the IR transmitter (e.g., laser or Xenon flash tube) and the detector receiver. Some open path IR sensors combine the emitter and detector into a single housing, and utilize a calibrated reflector placed in the field to establish the single line of sight of the system. Such sensors provide very limited coverage and rely on winds to carry gas emissions across the fixed IR path of the device. They also require precise and stable alignment of the transmitter and receiver (or reflector) assemblies. To create an optical detection line (sometimes referred to as a "fence") around an asset requires the installation of multiple such devices at significant expense, and this approach still relies on wind to transport gas through the line of an IR path. Moreover, such line sensors cannot localize the leak along the open sensing path, nor localize the source of the leak, nor quantify the emission flux. Thermal IR gas cameras suitable for gas leak detection and leak localization (single spectral band or multispectral) are available but are very expensive (US$100,000 or more). Such cameras detect and image methane and other hydrocarbons, but rely on the temperature difference between the gas and background objects in the scene. It is often the case that the gas emissions lack sufficient thermal contrast (particularly in cold weather outdoors) to reliably detect the gas. Due to the lack of thermal contrast, thermal IR gas cameras are not effective in detecting gas emissions through ground surface materials due to underground pipe leaks. Moreover, thermal IR gas cameras confuse water vapor and steam with gas and cannot reliably quantify emission flux.

Instead, the approaches described herein utilize multispectral imaging in the short-wave infrared (SWIR) spectral region. There are significant advantages in using a multispectral short-wave IR (SWIR) scanning sensor to image and quantify gas emissions. Such sensors do not rely on thermal contrast, and instead form imagery of gas based on the absorption of SWIR light provided in natural sunlight or by an artificial illuminator. They can also detect methane and other hydrocarbons in the presence of steam and water vapor, unlike thermal IR gas cameras. SWIR gas scanning imagers also cost significantly less than thermal IR gas cameras. A major limitation of previous SWIR systems is in operational range. In particular, when relying on artificial SWIR illumination reflecting off of natural materials in the environment, power requirements for the illuminator can range from typically 100 watts to many kilowatts and ranges of 50 m or more might not be achievable in practical applications.

Instead of relying in the reflectance of existing materials in a scene the approaches described herein leverage relatively inexpensive retro-reflective materials to significantly enhance the return of SWIR light from an illuminator back to an optical sensor (e.g., camera), thereby significantly extending the operational range of a SWIR sensor. Either the optical sensor (e.g., camera) or illuminator or both may be designed as scanning or non-scanning (see, for example, PCT Application No. PCT/US17/33157, entitled "Hydrocarbon Leak Imaging and Quantification Sensor" and filed May 17, 2017, PCT Application No. PCT/US18/22943, entitled "Scanning IR Sensor for Gas Safety and Emissions Monitoring" and filed Mar. 16, 2018, and PCT Application No. PCT/US18/50760, entitled "Systems and Methods for Multispectral Imaging and Gas Detection Using a Scanning Illuminator and Optical Sensor" and filed Sep. 12, 2018, the contents of each of which are hereby incorporated by reference in their entirety). In the case of a non-scanning SWIR camera utilizing optics of sufficient field of view to cover an area of interest, one implementation is to utilize a scanning SWIR illuminator in order to project light primarily along the reflective surfaces, thereby reducing the power requirements of the illuminator, e.g., a scanning SWIR searchlight illuminator. Such a scanning illuminator can be used in the presence of ambient SWIR illumination including solar illumination.

In certain embodiments, the systems and methods described herein are directed to a multi-platform system comprising one or more gas imaging sensors, one or more illuminators and one or more reflective surfaces, such that light projected from illuminators (e.g., the sun; e.g., one or more non-scanning illuminators, one or more scanning illuminators) may traverse an intervening gas cloud and, the light, being scattered back to the sensor by the reflective surface, being detected by at least one imaging sensor. In particular, in certain embodiments, the imaging sensor and illuminator can be used to create an "optical curtain" over a designated area.

Various embodiments of multispectral sensors and illuminators may be used in the tailored reflector installment approaches described herein. These include scanning multispectral SWIR imaging sensors and broadband scanning illuminators projecting structured beams of illumination (e.g., having planar striped beam patterns). Examples of these sensors are described in further detail in PCT Application No. PCT/US17/33157, entitled "Hydrocarbon Leak Imaging and Quantification Sensor" and filed on May 17, 2017, PCT Application No. PCT/US18/22943, entitled "Scanning IR Sensor for Gas Safety and Emissions Monitoring" and filed on Mar. 16, 2018, and, PCT Application No. PCT/US18/50760, entitled "Systems and Methods for Multispectral Imaging and Gas Detection Using a Scanning Illuminator and Optical Sensor" and filed on Sep. 12, 2018, the contents of each of which are hereby incorporated by reference in their entirety.

Such multispectral imaging sensors utilize optical sensors comprising one more detectors to detect light in a spectrally sensitive manner, over multiple spectral bands of interest. For example, in certain embodiments, optical sensors used to detect light in order to obtain multispectral absorption images as described herein may include multiple detectors (e.g., spectral detectors), each aligned and operable to detect light within a particular associated spectral band. As used herein, the term "detector", as used in reference to a detector of an optical sensor, refers to an individual detector element, such as a photodiode, or, in the context of a focal plane array, which comprises multiple detector pixels, a single detector pixel.

In such an optical sensor, each detector has its own individual detector instantaneous field of view (ifov), such that light from (e.g., emitted by and/or reflected by objects within) a scene and within a particular detector's individual ifov is captured, incident on the particular detector, and detected. The overall ifov of the optical sensor corresponds to the combined ifov of the individual detectors that it comprises. As used herein with respect to an optical sensor comprising multiple detectors, the term "instantaneous field of view (ifov)", as in a "sensor ifov", an "ifov of an optical sensor", and the like, refers to the overall ifov of the optical sensor, corresponding to the combined ifov of all the individual detectors that it comprises.

Optical sensors with multiple spectral detectors, capable of detecting light over multiple spectral bands of interest within the SWIR spectral region, can be designed in a variety of fashions. For example, as described in detail in PCT Application No. PCT/US17/33157, entitled "Hydrocarbon Leak Imaging and Quantification Sensor" and filed on May 17, 2017, PCT Application No. PCT/US18/22943, entitled "Scanning IR Sensor for Gas Safety and Emissions Monitoring" and filed on Mar. 16, 2018, and, PCT Application No. PCT/US18/50760, entitled "Systems and Methods for Multispectral Imaging and Gas Detection Using a Scanning Illuminator and Optical Sensor" and filed on Sep. 12, 2018, the contents of each of which are hereby incorporated by reference in their entirety, different arrangements of spectral filters and detector elements can be used to multiplex detection both spatially and spectrally depending on particular application requirements and cost considerations. For example, in certain embodiments, different spectral filters can be placed in front of each detector of an optical sensor, so that each detector is associated with and detects light within a different spectral band. For example, a two by two array of discrete photodetectors overlaid with a mosaic of four different spectral filters can be used to detect light within four different spectral bands from a single location. To create an image and obtain multispectral data from multiple locations, the optical sensor ifov can be scanned around a region, for example about the reflector installments described herein. In certain cases, multiple detectors can be used to detect light in different spectral bands, as well as from different spatial locations simultaneously, and avoid or reduce the need for scanning to create an image. For example, multiple linear photodetector arrays overlaid with different spectral filters, or similarly, two-dimensional focal plane array detectors overlaid with stripes of spectral filters can be used to image spatially along one dimension and spectrally along another, perpendicular, dimension. A two-dimensional image can then be obtained by scanning the sensor ifov over a single dimension. A two-dimensional FPA can also be used to obtain a two-dimensional multispectral image in the SWIR region, with multiple spectral filters positioned over different pixels of the FPA, similar to how visible cameras use a Bayer filter mosaic for visible color imaging.

As described in detail in PCT Application No. PCT/US17/33157, entitled "Hydrocarbon Leak Imaging and Quantification Sensor" and filed May 17, 2017, PCT Application No. PCT/US18/22943, entitled "Scanning IR Sensor for Gas Safety and Emissions Monitoring" and filed Mar. 16, 2018, and PCT Application No. PCT/US18/50760, entitled "Systems and Methods for Multispectral Imaging and Gas Detection Using a Scanning Illuminator and Optical Sensor" and filed Sep. 12, 2018, detecting light within multiple spectral bands can be used to determine absorption levels associated with spectral features indicative of (e.g., due to) particular hydrocarbon compounds of interest. In particular, in certain embodiments, at least a portion of the spectral bands of interest within which light is detected overlap with one or more spectral features of a particular compound of interest. In certain embodiments, at least one spectral band is used as a reference band, having few or only weak spectral features of the various compounds of interest. Comparing the intensity of light detected within a spectral band associated with a particular compound to the intensity of light within the reference band can be used to correct for factors such as spectral dependence of the illumination source, ambient environment absorption, and spectral dependence of materials off which light is reflected in order to be detected by the optical sensor. In this manner, differential optical depths representing absorption levels due to particular spectral features can be obtained, and used to detect and quantify presence of associated compounds of interest.

In certain embodiments, for example where ambient light (e.g., sunlight) is not sufficient, an illumination source is also used to provide artificial SWIR illumination. The illumination source may be a broadband source, producing illumination light having a spectral bandwidth spanning multiple spectral features of the various compounds of interest, for example having a bandwidth of 200 nanometers or more (e.g., 500 nanometers or more) in the SWIR region. The illumination source may be co-located with (but not necessarily mechanically coupled to) the optical sensor. In certain embodiments, the illuminator projects a beam of illumination that is scanned in a synchronized fashion with the ifov of the optical sensor, so as to maintain overlap between the projection of the sensor ifov and the beam of illumination. Overlap between the beam of illumination and the optical sensor can also be maintained by mechanically coupling the two.

For example, as described in detail in PCT Application No. PCT/US18/50760, entitled "Systems and Methods for Multispectral Imaging and Gas Detection Using a Scanning Illuminator and Optical Sensor" and filed Sep. 12, 2018, the illumination beam can be structured to provide a substantially uniform illumination spot that covers a portion of a target surface, such as a region of a reflector installment. In particular, the illumination beam can be structured to produce an illumination spot that has a long dimension (e.g., a length) that is substantially larger than the projection of ifov of the optical sensor onto the target surface. For example, the illumination spot may be a narrow, approximately rectangular stripe or ellipsoidal in shape. The ifov of the optical sensor can then be scanned, rapidly, along the length of the illumination spot (the fast axis), while both the ifov of the optical sensor and the illumination spot are scanned, together, at a slower rate in an approximately orthogonal direction (the slow axis). This allows the ifov of the optical sensor to be raster scanned across the scene, to form a multispectral absorption image.

Scanning of the illumination spot with the ifov of the sensor so as to maintain overlap between the two can be accomplished by using separate, synchronized scanners for slow scanning of the illumination spot and ifov. A single scanner, such as a rotational stage, on which both the illumination source and optical sensor along with its scanner (responsible for scanning along the fast axis) are mounted and maintained in fixed alignment, may also be used to maintain overlap and scan the illumination spot with the ifov along the slow axis.

Figure 1:
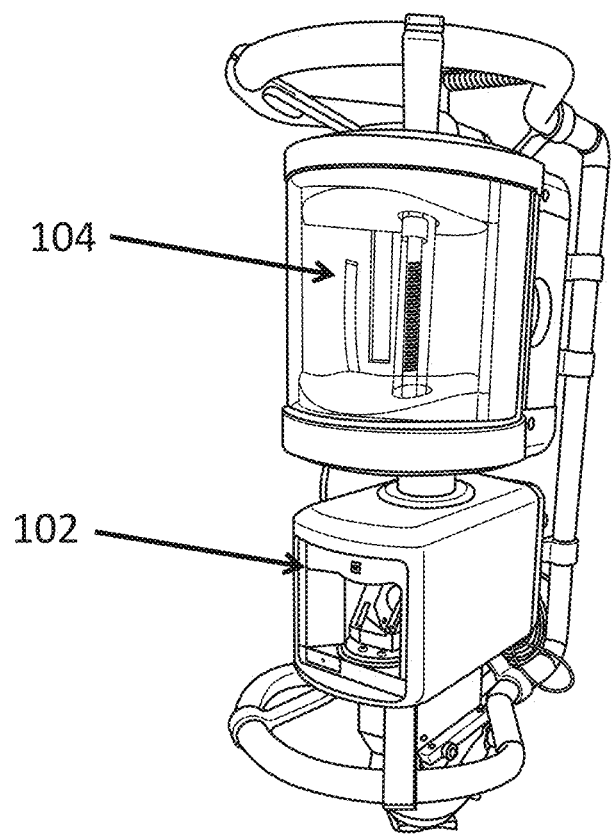
FIG. 1 is an image of a prototype multispectral short wave infrared (SWIR) scanning optical gas sensor and illuminator mounted in a protective cage, according to an illustrative embodiment.

An example scanning multispectral short-wave infrared (SWIR) optical sensor 102 and corresponding scanning SWIR illuminator 104 are shown in FIG. 1. This illuminator-sensor ensemble is able to form images of various hydrocarbon and other gases, including the greenhouse gases methane and carbon dioxide.

Figure 2A:
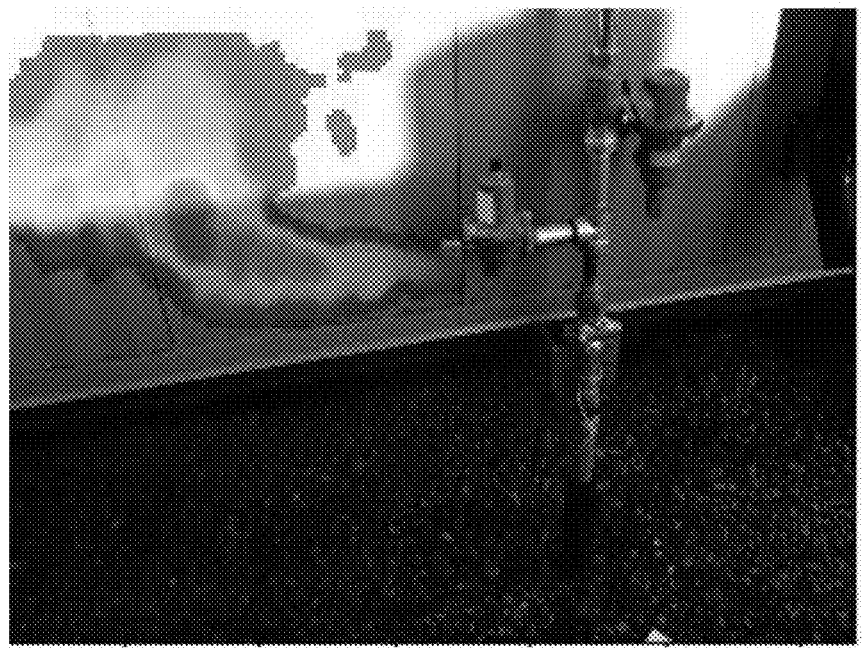
FIG. 2A is an example image showing SWIR absorption imagery of a natural gas leak overlaid on a visible camera image.
Figure 2B:
FIG. 2B is an example image showing SWIR absorption imagery of gas accumulation overlaid on a visible camera image.

SWIR gas imagery provides estimates of gas column density and emission flux for multiple types of emissions including high-pressure leaks (forming gas jets), low-pressure vents (forming plumes), surface emission patches (typical of underground gas pipe leaks), and extended area surface emissions. FIGS. 2A and 2B show examples of SWIR imagery as collected with the prototype of FIG. 1. FIG. 2A shows a 10 psig leak from a pressure relief valve outdoors in a scene with combined sunlight and shadow. FIG. 2B shows a gas cloud inside a gate station that accumulated near the ceiling. Furthermore, multiple scan paths can be used to create an "optical curtain" that envelopes an asset, such that any gas leaking from the asset must cross some area of this optical curtain, at which point it is detected via the spectral absorption of SWIR light forming the corresponding area of the optical curtain.

Figure 3:
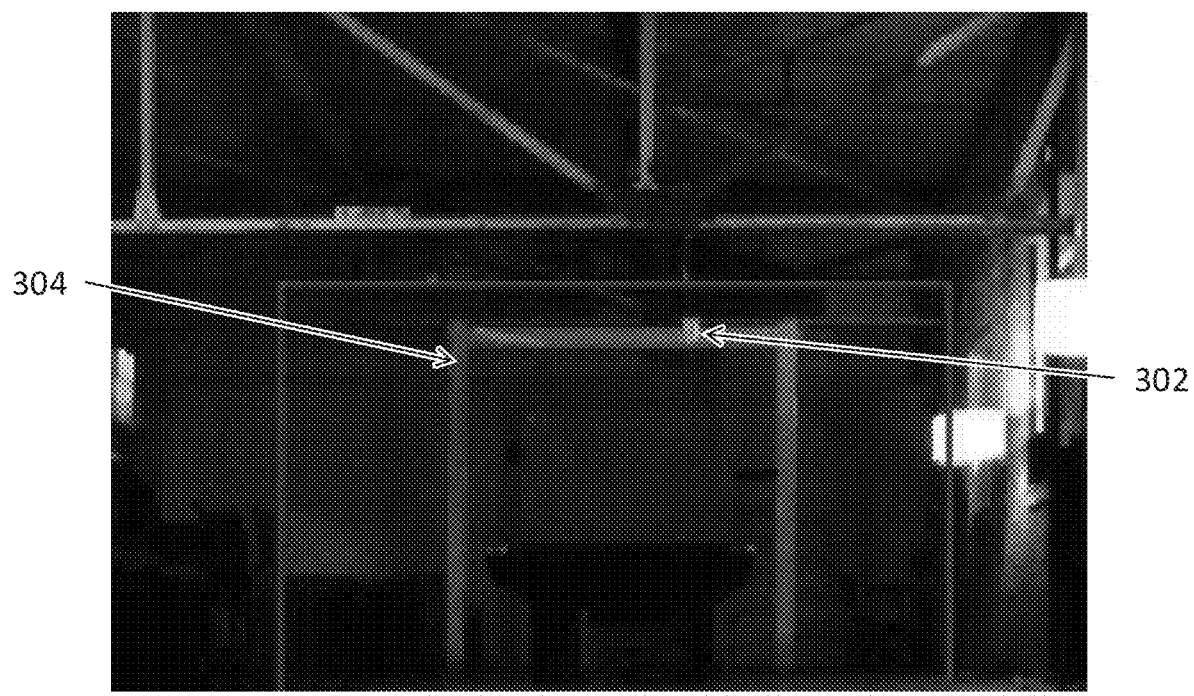
FIG. 3 is an image of an experimental reflector installment comprising a frame covered in retroreflective material that is scanned using the sensor embodiment shown in FIG. 1 to detect emission of gas, in accordance with an illustrative embodiment.

The approaches described herein strategically locate reflective materials, or preferably retro-reflective materials in the vicinity of assets to be monitored for gas leaks. An experimental setup illustrating an embodiment of this technology is shown in FIG. 3. A SWIR absorbing test card 302 located 6 meters in front of retro-reflective tape 304 (15 cm wide tape, forming a 3 meter arch) is detected by a SWIR scanning sensor and illuminator (e.g., FIG. 1), at a distance of 15 meters from the retro-reflective arch. This arch was clearly visible in the multispectral SWIR imagery at a range of 25 meters, using a 300 watt scanning illuminator. An imaging scan over a field of view of 60 degrees wide by 45 degrees high takes approximately 5 seconds. A full 360 degree scan would require only 30 seconds. Faster or slower scan times are possible with adjustment of system parameters.

Retro-reflective materials are engineered to return incident light back in a small cone around the incident light direction. They are typically fashioned from glass beads or prismatic reflectors resembling corner cubes acting as trihedral reflectors or by means of total internal reflection. Unlike a specular or mirror reflector, which scatters incident light primarily in accordance with Snell's law, and unlike a diffuse reflector which scatters incident light uniformly as a Lambertian scatterer, retro-reflective materials scatter light primarily back to where it came from. Retro-reflective materials can be fashioned in the form of sheets, rolls, and tapes. Retro-reflective materials are also available as paint, coating or ink (for example various products available from Prizmalite, GlowTec, Reflectionight™) or can be constructed out of available loose retro-reflective glass beads or spheres or crystals combined with some attachment method (e.g., an adhesive paste or tape) to an object. Retro-reflective materials can be made using glass beads and prismatic shapes from plastics and metal-coated plastics. Glass beads are typically used to make retro-reflective tapes, sheets, and paints, while prismatic shapes are often used to make retro-reflective tapes and sheets, but not paints. Retro-reflectors (e.g., corner cubes) can also be designed out of a range of reflective materials like polished aluminum, gold, or other metals. Moreover, retro-reflective materials are readily available from a variety of manufacturers (e.g., 3M High Intensity Prismatic Grade Reflective Sheeting 3930) and are inexpensive as they are used for a variety of applications such as transportation signage, safety markings, clothing for safety at night, as well as other related applications involving enhancing visibility at night (e.g., in lighted areas or from vehicle lights). Notably, while conventional applications of retro-reflector materials typically involve visible light, the reflector installment approaches described herein utilize retro-reflectors in an unconventional wavelength range, the SWIR.

A major advantage of using retro-reflective materials over reflective materials is that the material does not need to be precisely aligned towards the illuminator and optical sensor (e.g., camera). The incident angle of incoming SWIR light could be 30 degrees or more off the ideal perpendicular orientation and still allow for satisfactory operation of the detector system. This feature very significantly simplifies the installation of the reflector. In contrast, an installation of an open path detector system usually requires an angular precision of installation to within +/−0.5 degrees of perpendicular orientation between emitter and receiver. Moreover, the risk of mis-alignment of a reflector during operation is virtually eliminated. Use of retro-reflective materials as described herein also makes the reflector far less susceptible to problems arising from any vibrations of a surface to which such a reflector may be attached.

In certain embodiments, the approaches described herein utilize retro-reflectors in the SWIR part of the spectrum useful for detecting methane, other hydrocarbons, ammonia, and carbon dioxide. By mounting retro-reflective materials on posts, fences, crossbars, panels, walls, floors and other existing or custom installed structures (e.g., permanently installed, e.g., temporarily installed and relocatable), and scanning or imaging these materials with a multispectral short-wave infrared (SWIR) optical sensor while scanning these materials with a co-located SWIR illuminator (while possibly taking advantage of available solar illumination), an optical curtain is constructed that spans the area formed by the retro-reflective materials and the sensor.

FIG. 4 shows an example process 400 for detecting gas emission using the reflector installment technology described herein. As shown in the example process 400, an ifov of an optical sensor can be positioned towards a reflector installment 402 and light reflected from a plurality of locations along the installment detected in a spectrally sensitive manner, within one or more spectral bands of interest 404. Data corresponding to the detected light is received and/or accessed 406 by a processor of a computing device, and used to generate a spectral absorption map 408. The spectral absorption map can then be used to detect and/or quantify emission of leaking gas 410.

Figure 5A:
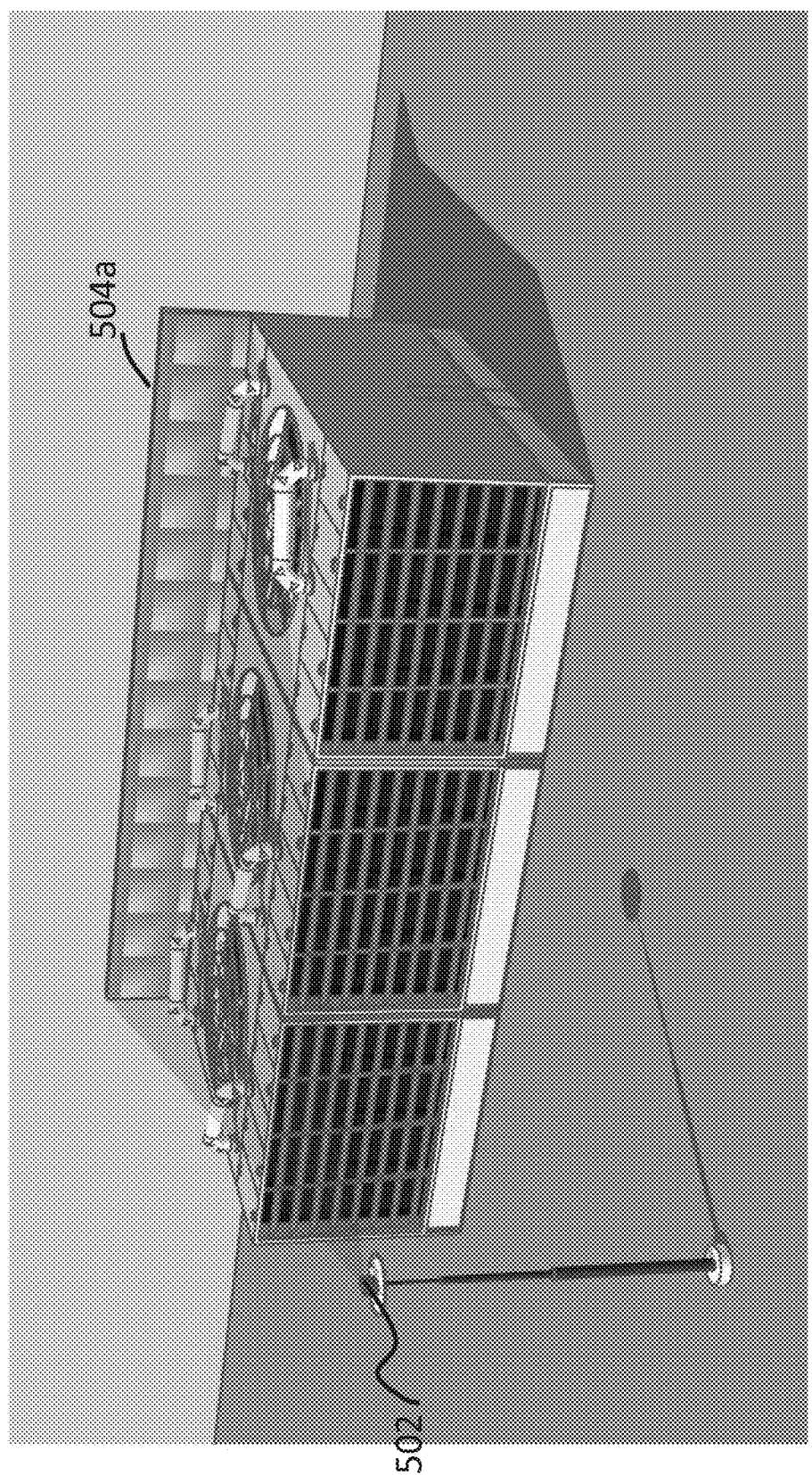
FIG. 5A is a schematic illustrating compressor coolers covered by a horizontal optical curtain formed via retro-reflective back panels and a scanning optical gas sensor and co-located illuminator, according to an illustrative embodiment.
Figure 5B:
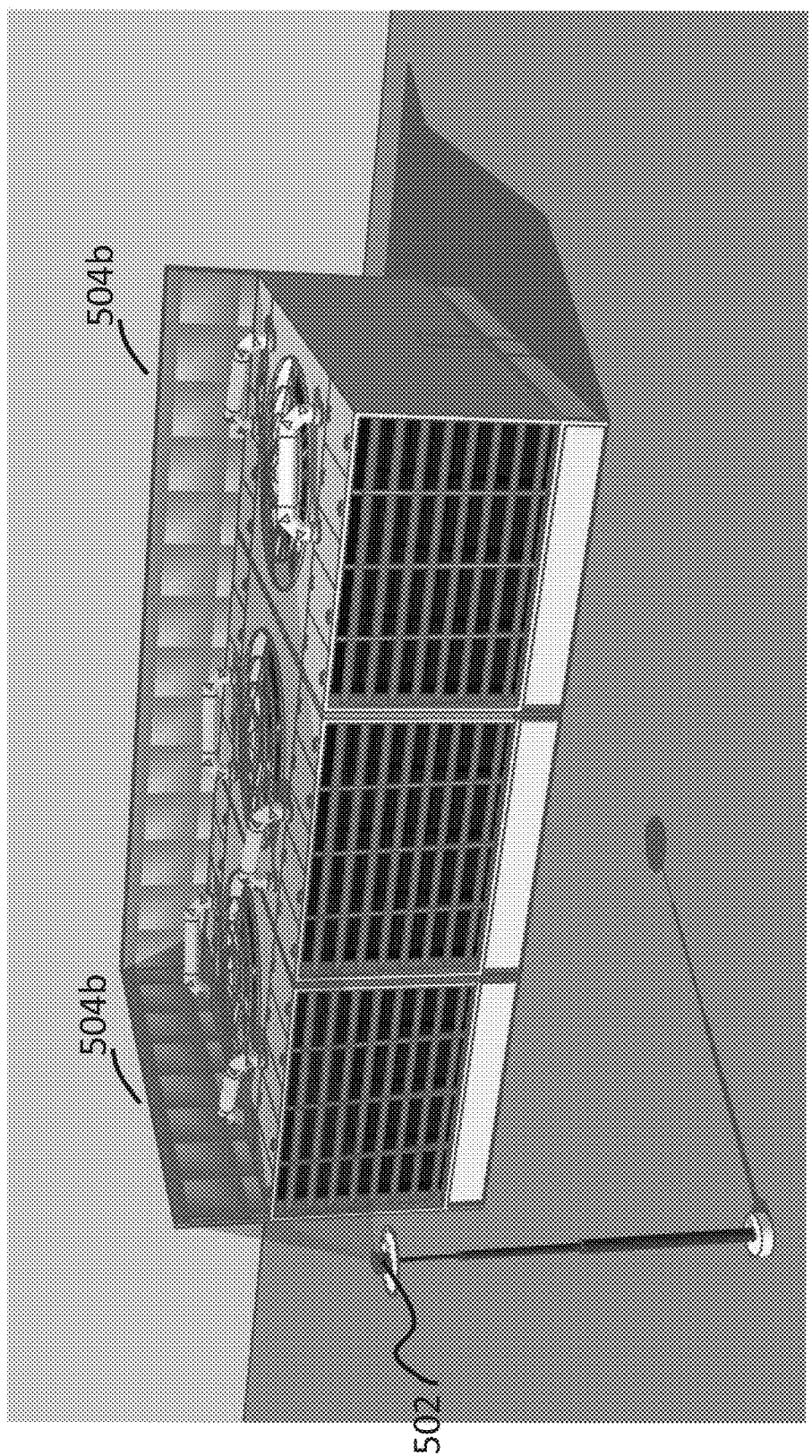
FIG. 5B is a schematic illustrating compressor coolers covered by a horizontal optical curtain formed via retro-reflective back and side panels and a scanning optical gas sensor and co-located illuminator, according to an embodiment.

FIGS. 5A-D provide illustrative embodiments of the described technology wherein compressor coolers are being monitored using an optical curtain formed using reflector installments (e.g., 504a, 504b, and 504c; in general, 504) arranged along the top and partially along the side and front of the compressor coolers. FIG. 5A shows compressor coolers covered by a horizontal optical curtain formed via retro-reflective back panels 504a and a scanning optical gas sensor and co-located illuminator 502, according to an illustrative embodiment. The co-located sensor and illuminator 502 are positioned in close proximity to each other, for example mounted next to or on top of each other. It is not necessary to strictly align and overlap the output beam from the illuminator with the returning beam that is detected by the optical sensor (e.g., shared optics for illuminator and sensor are not needed). FIG. 5B shows compressor coolers covered by a horizontal optical curtain formed via retro-reflective back and side panels 504b and a scanning optical gas sensor and co-located illuminator, according to an embodiment.

Figure 5C:
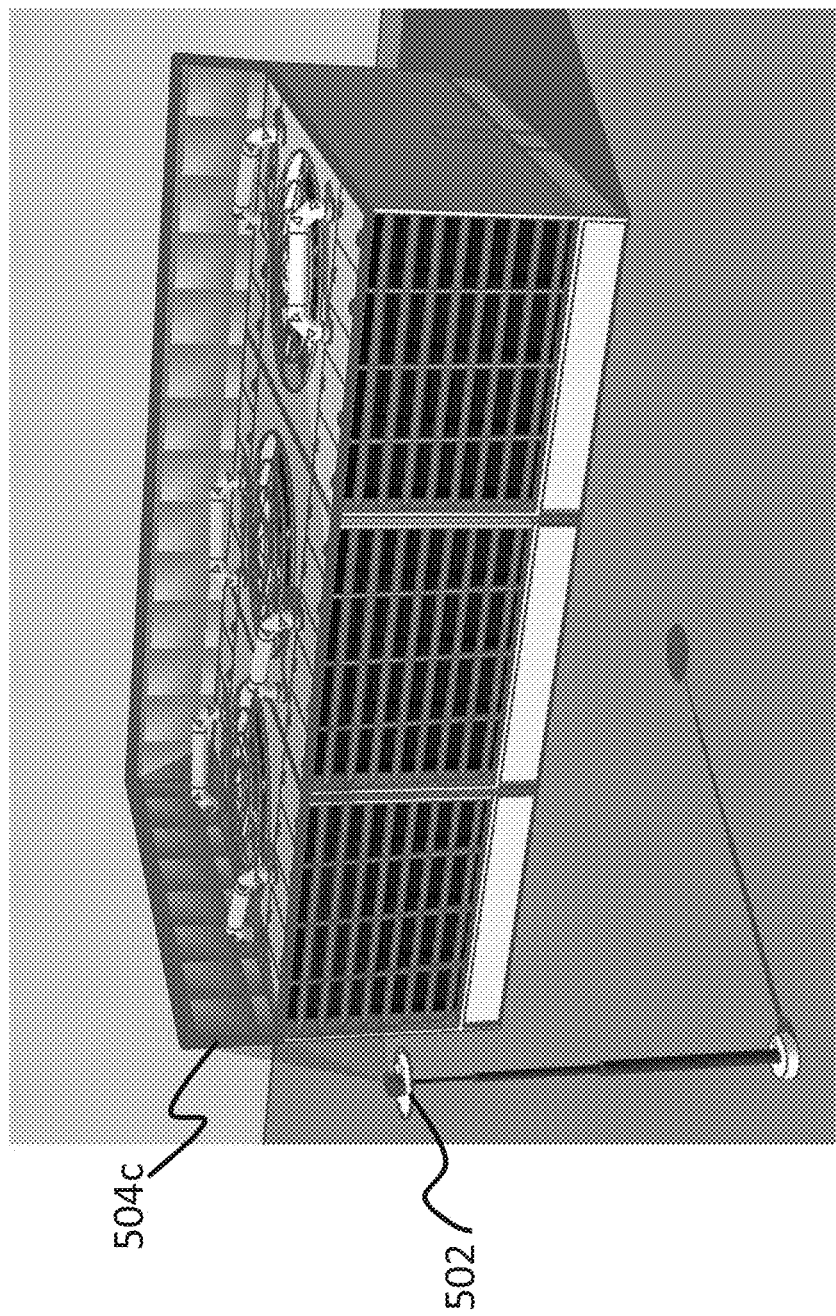
FIG. 5C is a schematic illustrating compressor coolers similar to those of FIG. 5B, with an optical curtain formed via retroreflective tape placed around a border of the tops of the compressor coolers and a scanning optical gas sensor and co-located illuminator, according to an illustrative embodiment.

FIG. 5C shows compressor coolers similar to those of FIG. 5B, with retro-reflective tape 504c placed around a border of the tops of the compressor coolers. In one embodiment, the retro-reflective tape is about 30 cm (12 inches) wide. Other widths of retro-reflective tape can also be used, however, in certain embodiment a narrowest dimension of a retro-reflective material should at least span an individual detector ifov. Since, in certain embodiments, the optical sensor comprises multiple spectral detectors (e.g., multiple pixels with different filters in front of each detector) an oversampling approach can be used to ensure that the entire ifov of each detector lands entirely on a narrow retro-reflector (e.g., a stripe or tape). For example, a detector ifov of 10 mrad produces a 25 cm projected spot at a distance of 25 m. Accordingly, sampling every 5 mrad or finer ensures that every individual spectral detector provides a full sample of the narrow reflector material as it scans across a scene. For a narrow vertically oriented strip of reflective material, horizontal oversampling is performed and, likewise, for a narrow horizontally oriented strip of reflective material, vertical oversampling is performed. This approach ensures that the retro-reflector material subtends the full ifov of each individual spectral detector of the optical sensor.

Figure 5D:
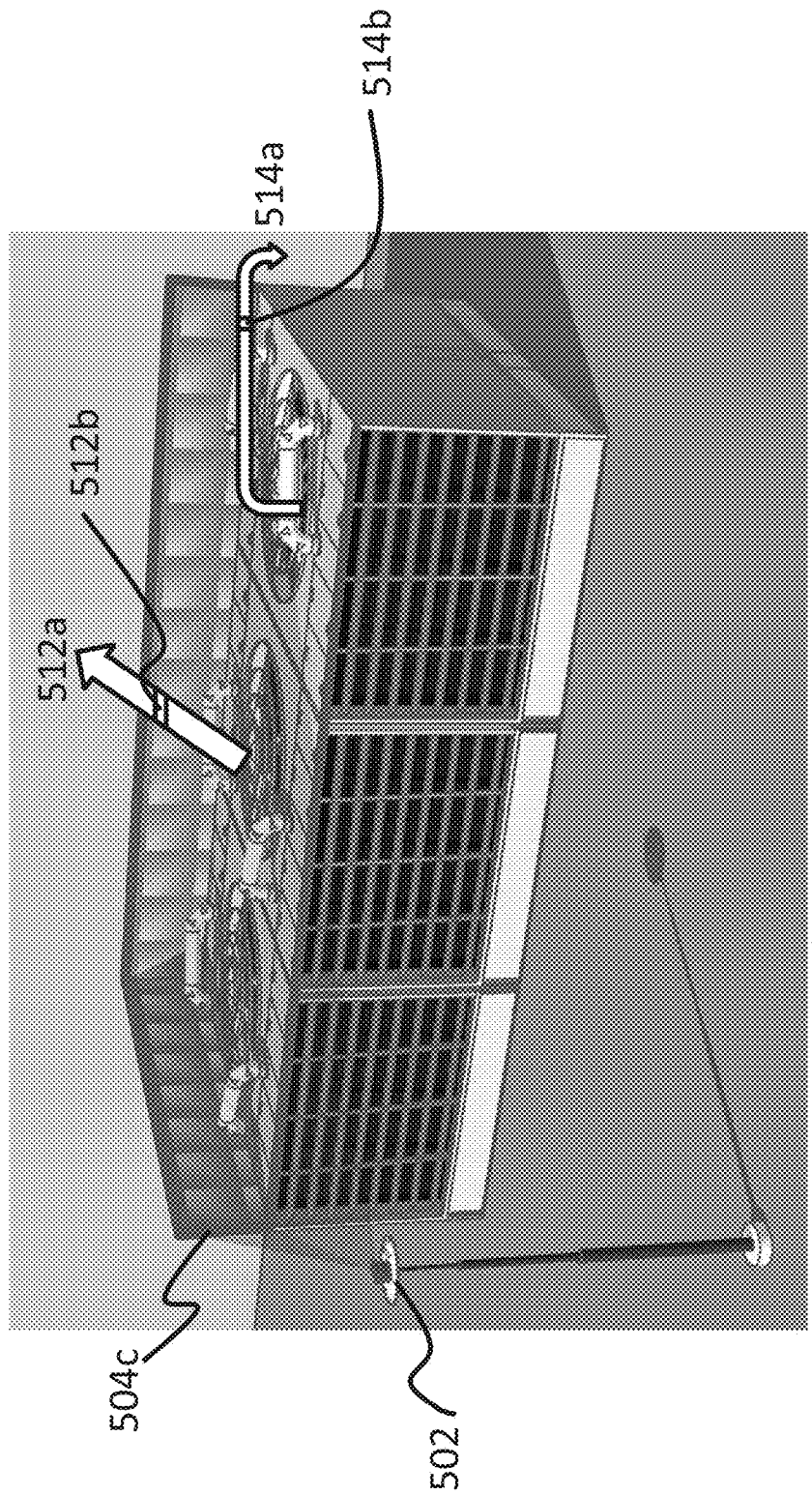
FIG. 5D is a schematic illustrating detection of gas emitted from the compressor coolers via the optical curtain formed by the retroreflective tape scheme shown in FIG. 5C, according to an illustrative embodiment.

As shown in FIG. 5C, a scanning optical gas sensor and co-located illuminator 502 illuminates the tape and detects light reflected back from the tape to form an optical curtain about the tops of the compressor coolers. Turning to FIG. 5D, gas emitted from the compressor coolers crosses the optical curtain and absorbs light traveling to and reflected from locations along the retro-reflective tape. In this manner, emission (e.g., corresponding to a leak or vent) can be detected and localized, and the spectrally sensitive nature of the detection methodology described herein allows for multiple particular hydrocarbon compounds to be identified based on the spectral bands in which they absorb. For example, as shown in FIG. 5D, rising methane gas 512a can be detected as it crosses 512b the top of the optical curtain. Volatile organic compounds (VOCs) 514a are heavier than air, and fall as they leak or vent. As illustrated in FIG. 5D, such VOCs can be detected as they cross 514b the side or the front of the optical curtain.

As illustrated in the figures, and, notably, an optical curtain is formed by the assembly of light rays emanating from a scanning illuminator, reflecting back from the retro-reflective panels or strips (e.g., comprised over many tiny retro-reflectors that cover extended strips or areas, as opposed to a few discreet corner cube reflectors that correspond to single points), to a scanning optical sensor that is nearly co-located with the scanning illuminator. This construct cannot be achieved using a scanning open path laser with a collection of discreet retro-reflecting corner cubes. The resulting optical curtain provided by the extended reflective surfaces used in the approaches described herein forms a surface in space that will detect gas crossing it. Optical curtains can be used to bound assets being monitored for emissions, and to divide space into sectors wherein gas crossing between these sectors will be detected.

Figure 6:
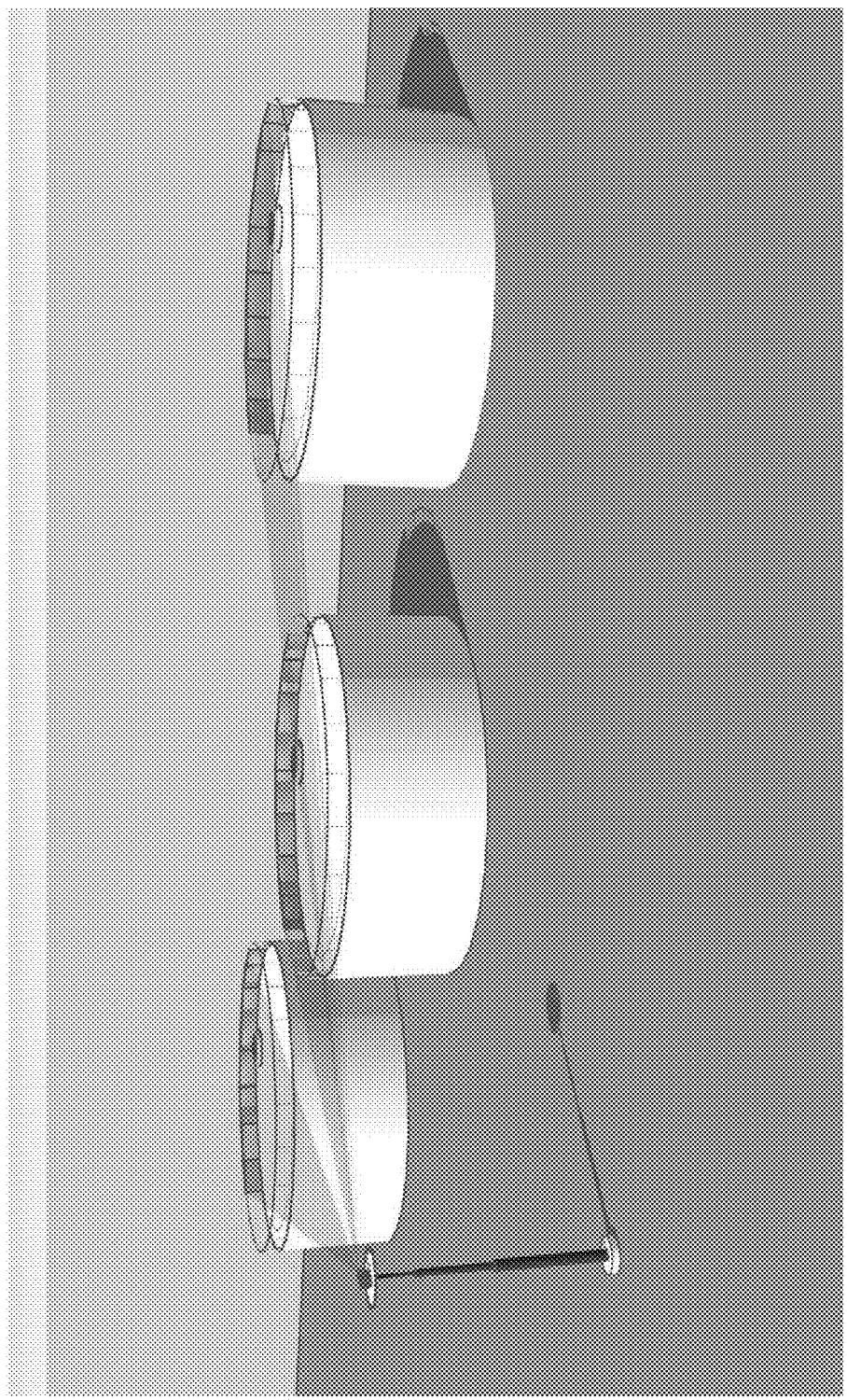
FIG. 6 is a schematic illustrating multiple tank hatches being monitored using retro-reflective panels mounted against railings along a perimeter of each tank hatch and a scanning optical gas sensor and co-located illuminator, according to an embodiment.

In certain embodiments, a single optical sensor and SWIR illuminator may be used to monitor multiple assets of interest. FIG. 6 shows an illustrative embodiment of a single system being used to monitor multiple fuel tanks using multiple optical curtains.

In certain embodiments, such optical curtains can also be constructed over the top and along the sides of assets to be monitored for gas leaks as illustrated in FIGS. 7A and 7B. A single sensor (e.g., camera) and SWIR illuminator may be used to monitor multiple areas of interest containing assets as well (e.g., as illustrated in FIGS. 8A and 8B). The sensed absorption of SWIR light at each line of sight along a scan provides an estimate of the density of the column of gas passing through that line of sight. Neighboring lines of sight along a scan provide for estimation of a total mass of gas crossing the optical curtain during a short interval of time (e.g., the time it takes for local wind to transport through the optical curtain the total mass estimated from SWIR absorption). For example, the technology could be used to quantify vented gas rising vertically (due to buoyancy and wind) through the top of the optical curtain (e.g., as in FIG. 8A) or dispersed horizontally through the side of the optical curtain (e.g., as in FIG. 8B) due to winds. Thus, combining this estimated mass from absorption at an optical curtain with estimates of gas motion induced by buoyancy and measured local wind speed and direction, enables the emission flux to be estimated.

The optical curtains formed by scanning reflector installments as described herein do not have to be continuous, but can also be formed from multiple segments (e.g., FIG. 6). Multiple segments can also be layered next to or on top of each other, or spaced apart at select locations. Segments can form a straight line or arbitrary 3-dimensional forms. Reflectors can form areas within portions of the field of view of the optical sensor (e.g., camera) and illuminator such as shown by the reflective blanket in FIG. 12. Reflectors may be installed on or as part of moveable structures or vehicles, for example to allow the temporary establishment of safety zones during plant commissioning and plant turnarounds or during repair operations indoors or outdoors. Emissions to be monitored might be released from individual locations such as shown in FIG. 7A, FIG. 7B, and FIG. 8. They may also be released as area emissions from underground or surface sources.

In certain embodiments, two or more optical sensors (e.g., cameras) may be used to envelop assets over their top and along multiple sides, and their intersecting lines of sight can be used to localize where gas passes through the optical curtain, helping to localize the source of the gas leak and to estimate the local gas concentration. FIG. 9 shows an illustrative embodiment of such an arrangement. Two optical sensor (e.g., camera)s with co-located SWIR illuminators and two sets of retro-reflective posts and crossbars form an optical curtain enclosing multiple tanks over top and on four sides localizes leaks and provide for estimates of leak concentration and emission flux. This can also be combined with estimates of gas motion induced by buoyancy and winds, providing an estimate of emission flux from a localized region through the optical curtain. This approach to localizing gas crossing an optical curtain formed by intersecting lines of sight is a form of tomography. Absorption sensed along lines of sight from one position of the scanning optical sensor can only determine the direction towards the gas leak, but not the distance to the gas. By intersecting lines of sight from multiple directions (e.g., from two or more scanning optical sensors), one can localize where the gas is crossing the optical curtain. Combining this location on the optical curtain with the measured local wind vector enables a gas plume to be traced back to its nearby source. Unlike gas dispersion modeling over long distances and large areas, using optical curtains to bound assets allows a simple extrapolation of gas detected on a curtain back to its source by reversing the direction of the wind vector.

Wind sensors can be incorporated into the systems and reflector installment approaches described herein in a variety of manners in order to allow wind measurements (e.g., speed and direct) to be obtained and used to localize and quantify leaks. For example, a directional wind sensor (e.g., an ultrasonic wind sensor) can be placed on an asset to be monitored. Ideally, the wind sensor is placed as close to a vent or potential leak points as possible. In certain embodiments, placing a wind sensor on an asset in this manner is not practical or cost effective, especially for example when monitoring multiple assets around a facility with many vents and many possible leak points. In such cases, a wind sensor can be mounted on a mast above or near the scanning optical sensor and illuminator, and the measured speed at the location of the optical sensor/illuminator can be used when quantifying a detected leak. In certain embodiments, measurements from multiple wind sensors located around a facility (e.g., at four corners of a facility and atop the scanning optical sensor and illuminator) can be combined with models of wind flow (e.g., a dynamical model) through the facility in order to estimate wind speed and direction at any time at each potential leak location. In certain embodiments, the operating range of optical sensor (e.g., camera) with co-located SWIR illuminator is at least 50 meters, though a range of 100 meters is desirable. Mounted at a height of, for example, 10-15 meters, the sensor system could monitor large compressors and tank farms (e.g., FIGS. 10A and 10B). With the optical sensor (e.g., camera) and co-located illuminator mounted centrally in a facility at a height above the tallest structure, it is possible to monitor a facility of 100 meter scale or more. Multiple optical sensors (e.g., cameras) and SWIR Illuminators can be configured around a large facility in combination with strategically located retro-reflective posts and crossbars to create optical curtains that cover large areas of assets to monitor for gas leaks.

In the prototype SWIR sensor shown in FIG. 1, the sensor is of the scanning type and the ifov (angle subtended by a single spectral band detector of the multispectral sensor) is 10 milliradians. Thus, the footprint of a single detector channel (and thereby the reflector dimension representing a single pixel) is 25 cm at a distance of 25 m, and 50 cm at a distance of 50 m. By doubling the focal length of the objective lens, the size of the optical footprint can be reduced by half. By trading off lens focal length, illumination power, and exposure time of the sensor, it is possible to increase operating range while keeping the size of the retro-reflective materials to an easy to install and cost-effective width (e.g., 1 to 50 cm). As described herein, the minimum size of a reflective patch or segment should be matched to the individual ifov of a single SWIR detector. Larger size reflectors provide additional signal to form additional pixels at the sensor, so can serve to enhance sensitivity and confidence in the detection of gas emissions.

The scan pattern of the SWIR illuminator and sensor across the installed reflectors can be set to trace out an optical curtain, but also automatically adjust itself to repeat scan select spots or segments of reflectors in order to increase confidence of possible gas detections, improve localization of detected emissions, and improve estimated emission flux. Similar intelligent scanning strategies are described, for example, in PCT Application No. PCT/US18/22943, entitled "Scanning IR Sensor for Gas Safety and Emissions Monitoring" and filed Mar. 16, 2018, the content of which is hereby incorporated by reference in its entirety.

An optical sensor (e.g., camera) and illuminator will typically be configured to cover the entire field of view formed by the reflectors at an outermost distance. For example, a optical sensor (e.g., camera) with a technical field of view of 60 degrees×45 degrees may be configured to scan a fraction of its vertical and horizontal field of view (for example, 40 degrees×30 degrees); however, this fractional field of view will cover an area that is substantially larger than the field of view covered by retro-reflective material. In one preferred embodiment the illuminator will be of a scanning type in order to reduce the required power demand for a given target distance. In another embodiment, the field of regard of the illuminator and optical sensor (e.g., camera) will be configured such as to only observe areas where the reflective materials installed, while the optical sensor (e.g., camera) senses primarily the retro-reflected light. In any scanning implementation of either optical sensor (e.g., camera) or illuminator, the scanning (if any) by the sensor must be synchronized with the scanning (if any) of the illuminator over the reflective surfaces.

For a sensed field of view subtending 60 degrees horizontally by 45 degrees vertically, a low-resolution (e.g., 10 millirad ifov) image would comprise approximately 100 columns and 75 rows (i.e., 7500 pixels), while an optical curtain created from two vertical reflective posts and one reflective crossbar would comprise approximately 250 pixels. This small amount of data can be rapidly processed in real-time in order to detect gas absorption along these 250 lines of sight, and be used to rapidly control an intelligent adaptive scanning pattern. Also possible are smaller optical curtains encompassing only for example 10, 20 or 50 pixels, optical curtains that are of curved shape as well as optical curtains directed at only one or two sides adjacent to an asset (as opposed to three or all four sides). Similarly, the same scanning optical sensor and co-located scanning illuminator may scan multiple assets located around a site, but in various directions from an installed sensor mast. Thus, it is quite possible to acquire multispectral absorption data along some thousands of lines of sight.

In order to cover large interiors of enclosed or semi-enclosed spaces, the sensor and illuminator may be mounted on a rotating platform suspended from the ceiling of the interior space. Installing reflective surfaces along the walls near the ceiling enables the sensing system to monitor the space beneath the ceiling, e.g., for the presence of gas due to a leak inside the space (as shown in FIG. 11 or a larger area inside the room).

In a certain embodiment, the SWIR illuminator projects a narrow beam approximately matched to the narrow dimension of the installed reflective surfaces (which, as described herein, is also approximately matched to the size of the ifov's of the individual detectors of the optical sensor), and scans along the retro-reflective surfaces in a searchlight pattern (e.g., the illuminator projects a circular beam of diameter at the range of the reflectors equal to the width of a narrow reflective strip or segment, the illuminator being scanned by a pan-tilt unit). The SWIR sensor is required to sense the corresponding locations being illuminated by the scanned searchlight illuminator. In the case of a scanning SWIR sensor, the scan can cover an entire field of view as long as it senses the reflective surfaces in synchrony with their illumination. In the case of a staring focal plane array SWIR camera, full imagery collected at video rate can detect the reflected light from the scanning searchlight illuminator.

In certain embodiments, the technology may be modular or portable in nature as shown in the illustrative embodiment of FIG. 12. FIG. 12 shows monitoring the process of LNG transfer onto a vessel using a retro-reflective blanket 1202 mounted around the vessel's fueling portal, and a nearby scanning optical gas sensor with co-located illuminator 1204 having line of sight to the fueling portal. The scanning optical sensor (e.g., camera) and illuminator assembly is mounted to a mobile unit that allows for the assembly to be transported to the desired area for temporary use. The retro-reflective blanket may be either temporary or permanently affixed to the area to be monitored. Similarly, relocatable reflectors, illuminators, and sensors can be used at temporary work sites such as outdoor repair operations of above ground and underground gas and oil infrastructure, and for plant commissioning and plant turnarounds.

The technology described herein has application (but is not limited to) to monitoring assets throughout the oil and gas industry, the petrochemical and heavy industries, pulp and paper, other producing industries, coal mining, utilities, agriculture, and science. It is suitable for use in environments that are outdoors, indoors, onshore, and offshore. Thus, the technology has implications for both environmental and safety monitoring applications. A partial list of emissions monitoring applications includes, without limitation:

Well pad "tenting" near residences and townships;

Fracking well and rig monitoring for detection of gas and oil spray during operations;

Outdoor monitoring of emissions from gas plants and refinery operations;

Outdoor monitoring of emissions from compressors and compressor coolers;

Monitoring of oil battery tanks and associated equipment, for example highly toxic hydrogen sulfide gas may be associated with the presence of methane;

Indoor monitoring of facility ceilings for methane gas accumulation and clouds;

LNG transfer operations on land monitoring for spillage and vaporization;

LNG tanker transfer operations at sea monitoring for spillage and vaporization;

Floating LNG plant operations at sea;

LNG ship engine room monitoring for gas leaks;

Offshore oil and gas platform assets monitoring for leaks and venting;

Relocatable monitoring of heavy oil production wells that intermittently vent gas;

Relocatable monitoring for leaks during plant commissioning and turnarounds;

Relocatable monitoring for leaks during repair operations of above ground oil and gas infrastructure;

Relocatable monitoring for leaks during repair operations of underground oil and gas pipelines and infrastructure;

Relocatable or installed monitoring of areas such as landfills, industrial plants, pipelines, $CO_2$ reinjection assets, or perma-frost for surface emissions of gases;

Monitoring for surface emissions in coalmines, bitumen, or oil sand monitoring applications;

Monitoring of Methane emissions from Hog farms and agricultural installations;

Monitoring of Ammonia emissions, for example during fertilizer production;

Monitoring of Ethylene emissions in storage facilities, petrochemical plants, and refineries;

Replacement of so called "fence line monitoring" that is currently performed by open-path line detectors with optical curtains that bound the volume of space; and Monitoring of off-shore oil and gas drilling, loading, and processing installations.

Example 1. Demonstration of Gas Detection Via a Three Sided Optical Curtain

This example demonstrates detection of gas via a three sided optical curtain. FIG. 15A shows a visible camera image of a scene comprising a pipe 1502 releasing gas and a retro-reflector installment used to create the optical curtain. The pipe 1502 is a 2 inch vent pipe leaking at a rate of approximately 20 standard cube feet per hour (SCFH). The reflector installment includes a frame 1506 having retroreflective surfaces mounted behind the pipe. 3M High Intensity Prismatic Grade Reflective Sheeting 3930 is used as the retro-reflective surface. A scanning optical sensor and illuminator directs light to locations about the retro-reflective frame 1506 and detects light reflected back to the detector, thereby forming a three-sided optical curtain. The visible camera image of FIG. 15A is taken from the vantage point of the optical sensor and illuminator, which are situated a distance of about 5 meters from the pipe 1502 and 7 m from the retroreflective frame 1506. By virtue of the three-sided optical curtain formed using the retro-reflective frame 1506, any gas that crosses the sides of the optical curtain can be detected. For example, the image in FIG. 15A is overlaid with a false color optical absorption image that allows leaking gas to be visualized based on spectral imaging data. As can be seen, a region of gas 1508 crossing a side of the optical curtain, in front of the retroreflective frame 1506 is readily detected. The detected gas 1508 is about [internal note: the reflected gas cloud likely will have a depth to it and in principle can be anywhere between the retroreflective frame and the sensor as we are measuring column density] 1 meter to the side. In this example, a reflector panel 1504 is also placed behind the release point, and a plume of gas 1510 about 1 meter behind the release location can be observed. The reflector placed behind the release location is not required, and is used in this example for illustrative purposes, to validate the detection of the leaking gas by the optical curtain formed using retro-reflector frame 1506 and to illustrate the direction of the gas plume. Accordingly, this example shows that the systems and methods described herein can be used to detect leaks using only a narrow strip of nearby reflectors, without reflectors located behind the action leak location. Moreover, by using measurements of wind speed the source of the leak can be localized, and leak rate can be quantified. In particular, FIG. 15B shows how wind direction influences the gas plume, and the resulting absorption image formed as it passes through the optical curtain. For example, as described herein, estimates of wind direction can be combined with measurements of gas at locations along optical curtains (e.g., formed via multiple viewing directions) to localize leaks via simplified extrapolation along a vector, without necessarily requiring complex dispersion modelling.

Example 2. Demonstration of Gas Detection at 20 Meters

Example 2 demonstrates gas detection at a distance of 20 meters using 3M 3930 retro-reflectors positioned behind a gas leak source. FIG. 16 shows a visible camera image of a room with an absorption image overlaid showing levels of absorption in false color. As shown in the figure, leaking gas can be seen in a region 1602a at the back of the room (inside a fume hood). An expanded view 1602b of the region shows the detected gas leak in greater detail. Accordingly, this example shows how a single, or small number of strategically positioned retro-reflectors can be used to detect gas leaks at tens of meters using a scanning multispectral optical sensor and co-located scanning (broadband) illuminator.

Example 3. Rapid Scanning Over a Wide Field of View

This example demonstrates how the tailored retro-reflector installment approaches described herein can be used to allow for large fields of view to be scanned rapidly. An example is an installation using discontinuous reflectors at an oil well as depicted in FIG. 18. Such a well may typically include one or several pump jacks, measurement equipment, a separator, and tanks. A retro-reflector panel or retro-reflector stripe may be each placed behind pump jack, a separator (or, for example, in the case of an enclosed separator behind a relief vent, on top of such separator enclosure), behind measurement equipment, and behind any pressure relief valve or hatch on top of a tank. For example, in FIG. 18, four separated locations to be monitored: storage tanks (pressure relief valves and thief hatches), a compressor shed (roof vents), a separator tank roof (vent), and pump jacks are shown. It is noted that in an installation the retro-reflector might be placed around or behind the asset to be monitored and it may be partially visually obscured from the point of view of the optical sensor (e.g., camera) (due to reasons of ease of installation). From the viewpoint of the optical sensor (e.g., camera) and depending on the specific installation the retro-reflector panels might visually form one-, two-, three- or four-sided optical curtains around the asset due to part of the panel being partially visually obscured. The optical sensor (e.g., camera) and illuminator may scan the four or more retro-reflector arrays in a discontinuous fashion. For example, slow scanning across one reflector panel or stripe, then fast movement to the beginning of the second panel or stripe followed by slow scanning across this second panel or stripe and so on. This approach minimizes the response time to detect a leak by maximizing the amount of time data is collected in front of retro-reflectors as opposed to sections in the field of view without retro-reflectors.

Example 4. Angular Dependence of Reflectivity of Retro-Reflector Materials

FIG. 17 shows measurement results of the angle dependence of light retro-reflection of 3M Engineer Grade Prismatic Reflective Sheeting 3430 in the 2250 nm-2350 nm band, in which the illuminator and spectral sensor were approximately co-located. Data was measured from a 20 m distance. It can be seen that the percentage of light received drops steadily with increasing angle of incidence of the light onto the retro-reflector. At an angle of 45 degrees approximately 27.5% of the light is received back at the sensor relative to 100% at 0 degrees.

Notably, retro-reflector materials are conventionally used for visible light applications, and specifications from manufactures show data for visible light. The measurement provided in this example, for the 2250 to 2350 nm band within the SWIR region show that available retro-reflector materials can be used to operate out to angles of 45 degrees away from perpendicular to a reflector panel. In certain embodiments, to maximize the sensitivity of a measurement the reflector panels can be angled such as to keep them within a limit of for example 10 degrees (or whatever threshold angle is deemed maximally permissible given a desired detection sensitivity).

Computer System and Network Environment

As shown in FIG. 13, an implementation of a network environment 1300 for use in providing systems and methods described herein is shown and described. In brief overview, referring now to FIG. 13, a block diagram of an exemplary cloud computing environment 1300 is shown and described. The cloud computing environment 1300 may include one or more resource providers 1302a, 1302b, 1302c (collectively, 1302). Each resource provider 1302 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1302 may be connected to any other resource provider 1302 in the cloud computing environment 1300. In some implementations, the resource providers 1302 may be connected over a computer network 1308. Each resource provider 1302 may be connected to one or more computing device 1304a, 1304b, 1304c (collectively, 1304), over the computer network 1308.

The cloud computing environment 1300 may include a resource manager 1306. The resource manager 1306 may be connected to the resource providers 1302 and the computing devices 1304 over the computer network 1308. In some implementations, the resource manager 1306 may facilitate the provision of computing resources by one or more resource providers 1302 to one or more computing devices 1304. The resource manager 1306 may receive a request for a computing resource from a particular computing device 1304. The resource manager 1306 may identify one or more resource providers 1302 capable of providing the computing resource requested by the computing device 1304. The resource manager 1306 may select a resource provider 1302 to provide the computing resource. The resource manager 1306 may facilitate a connection between the resource provider 1302 and a particular computing device 1304. In some implementations, the resource manager 1306 may establish a connection between a particular resource provider 1302 and a particular computing device 1304. In some implementations, the resource manager 1306 may redirect a particular computing device 1304 to a particular resource provider 1302 with the requested computing resource.

FIG. 14 shows an example of a computing device 1400 and a mobile computing device 1450 that can be used to implement the techniques described in this disclosure. The computing device 1400 is intended to represent various forms of digital computers, such as laptops, desktops, workstations, personal digital assistants, servers, blade servers, mainframes, and other appropriate computers. The mobile computing device 1450 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1400 includes a processor 1402, a memory 1404, a storage device 1406, a high-speed interface 1408 connecting to the memory 1404 and multiple high-speed expansion ports 1410, and a low-speed interface 1412 connecting to a low-speed expansion port 1414 and the storage device 1406. Each of the processor 1402, the memory 1404, the storage device 1406, the high-speed interface 1408, the high-speed expansion ports 1410, and the low-speed interface 1412, are interconnected using various busses, and may be mounted on a common motherboard or in other manners as appropriate. The processor 1402 can process instructions for execution within the computing device 1400, including instructions stored in the memory 1404 or on the storage device 1406 to display graphical information for a GUI on an external input/output device, such as a display 1416 coupled to the high-speed interface 1408. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 1404 stores information within the computing device 1400. In some implementations, the memory 1404 is a volatile memory unit or units. In some implementations, the memory 1404 is a non-volatile memory unit or units. The memory 1404 may also be another form of computer-readable medium, such as a magnetic or optical disk.

The storage device 1406 is capable of providing mass storage for the computing device 1400. In some implementations, the storage device 1406 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1402), perform one or more methods, such as those described above. The instructions can also be stored by one or more storage devices such as computer- or machine-readable mediums (for example, the memory 1404, the storage device 1406, or memory on the processor 1402).

The high-speed interface 1408 manages bandwidth-intensive operations for the computing device 1400, while the low-speed interface 1412 manages lower bandwidth-intensive operations. Such allocation of functions is an example only. In some implementations, the high-speed interface 1408 is coupled to the memory 1404, the display 1416 (e.g., through a graphics processor or accelerator), and to the high-speed expansion ports 1410, which may accept various expansion cards (not shown). In the implementation, the low-speed interface 1412 is coupled to the storage device 1406 and the low-speed expansion port 1414. The low-speed expansion port 1414, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1400 may be implemented in a number of different forms, as shown in the figure. For example, it may be implemented as a standard server 1420, or multiple times in a group of such servers. In addition, it may be implemented in a personal computer such as a laptop computer 1422. It may also be implemented as part of a rack server system 1424. Alternatively, components from the computing device 1400 may be combined with other components in a mobile device (not shown), such as a mobile computing device 1450. Each of such devices may contain one or more of the computing device 1400 and the mobile computing device 1450, and an entire system may be made up of multiple computing devices communicating with each other.

The mobile computing device 1450 includes a processor 1452, a memory 1464, an input/output device such as a display 1454, a communication interface 1466, and a transceiver 1468, among other components. The mobile computing device 1450 may also be provided with a storage device, such as a micro-drive or other device, to provide additional storage. Each of the processor 1452, the memory 1464, the display 1454, the communication interface 1466, and the transceiver 1468, are interconnected using various buses, and several of the components may be mounted on a common motherboard or in other manners as appropriate.

The processor 1452 can execute instructions within the mobile computing device 1450, including instructions stored in the memory 1464. The processor 1452 may be implemented as a chipset of chips that include separate and multiple analog and digital processors. The processor 1452 may provide, for example, for coordination of the other components of the mobile computing device 1450, such as control of user interfaces, applications run by the mobile computing device 1450, and wireless communication by the mobile computing device 1450.

The processor 1452 may communicate with a user through a control interface 1458 and a display interface 1456 coupled to the display 1454. The display 1454 may be, for example, a TFT (Thin-Film-Transistor Liquid Crystal Display) display or an OLED (Organic Light Emitting Diode) display, or other appropriate display technology. The display interface 1456 may comprise appropriate circuitry for driving the display 1454 to present graphical and other information to a user. The control interface 1458 may receive commands from a user and convert them for submission to the processor 1452. In addition, an external interface 1462 may provide communication with the processor 1452, so as to enable near area communication of the mobile computing device 1450 with other devices. The external interface 1462 may provide, for example, for wired communication in some implementations, or for wireless communication in other implementations, and multiple interfaces may also be used.

The memory 1464 stores information within the mobile computing device 1450. The memory 1464 can be implemented as one or more of a computer-readable medium or media, a volatile memory unit or units, or a non-volatile memory unit or units. An expansion memory 1474 may also be provided and connected to the mobile computing device 1450 through an expansion interface 1472, which may include, for example, a SIMM (Single In Line Memory Module) card interface. The expansion memory 1474 may provide extra storage space for the mobile computing device 1450, or may also store applications or other information for the mobile computing device 1450. Specifically, the expansion memory 1474 may include instructions to carry out or supplement the processes described above, and may include secure information also. Thus, for example, the expansion memory 1474 may be provide as a security module for the mobile computing device 1450, and may be programmed with instructions that permit secure use of the mobile computing device 1450. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 1452), perform one or more methods, such as those described above. The instructions can also be stored by one or more storage devices, such as one or more computer- or machine-readable mediums (for example, the memory 1464, the expansion memory 1474, or memory on the processor 1452). In some implementations, the instructions can be received in a propagated signal, for example, over the transceiver 1468 or the external interface 1462.

The mobile computing device 1450 may communicate wirelessly through the communication interface 1466, which may include digital signal processing circuitry where necessary. The communication interface 1466 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1468 using a radio-frequency. In addition, short-range communication may occur, such as using a Bluetooth®, Wi-Fi™, or other such transceiver (not shown). In addition, a GPS (Global Positioning System) receiver module 1470 may provide additional navigation- and location-related wireless data to the mobile computing device 1450, which may be used as appropriate by applications running on the mobile computing device 1450.

The mobile computing device 1450 may also communicate audibly using an audio codec 1460, which may receive spoken information from a user and convert it to usable digital information. The audio codec 1460 may likewise generate audible sound for a user, such as through a speaker, e.g., in a handset of the mobile computing device 1450. Such sound may include sound from voice telephone calls, may include recorded sound (e.g., voice messages, music files, etc.) and may also include sound generated by applications operating on the mobile computing device 1450.

The mobile computing device 1450 may be implemented in a number of different forms, as shown in the figure. For example, it may be implemented as a cellular telephone 1480. It may also be implemented as part of a smart-phone 1482, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, modules described herein can be separated, combined or incorporated into single or combined modules. Any modules depicted in the figures are not intended to limit the systems described herein to the software architectures shown therein.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein. Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method of detecting emission of gas comprising one or more compounds of interest, the method comprising:
   (a) positioning an instantaneous field of view (ifov) of an optical sensor toward a reflector installment mounted about a site to be monitored, wherein the reflector installment comprises one or more continuous reflective sections, wherein each continuous reflective section: (i) comprises a retroreflective panel mounted on and/or retroreflective material affixed to a pre-existing structure in proximity to and behind, with respect to a location of the optical sensor, one or more assets to be monitored for gas emission, (ii) is oriented vertically with respect to a plane passing through the optical sensor and above the site, and (iii) is of sufficient size to span a plurality of sampled locations;
   (b) detecting, with one or more detectors of the optical sensor, light within one or more spectral bands of interest, the detected light having been reflected from a plurality of sampled locations on the reflector installment and captured within the ifov of the optical sensor, wherein at least a portion of the one or more spectral bands of interest overlap with one or more spectral features associated with the one or more compounds of interest;
   (c) receiving and/or accessing, by a processor of a computing device, data corresponding to the detected light reflected from the plurality of sampled locations;
   (d) determining, by the processor, for each of the plurality of sampled locations, an absorption level associated with at least one of the one or more spectral features using the detected light, thereby generating a spectral absorption map comprising a plurality of absorption levels, each associated with a particular sampled location and spectral feature; and (e) detecting the emission of the gas from within the site to be monitored using the generated spectral absorption map.

2. The method of claim 1, comprising:
directing a beam of illumination from an illumination source and toward the reflector installation; and
scanning the beam of illumination across at least a portion of the reflector installation, thereby illuminating the plurality of sampled locations.

3. The method of claim 2, comprising scanning the beam of illumination in a continuous fashion across a portion of a target region comprising the reflector installation, thereby illuminating the plurality of sampled locations along the reflector installation as well as other locations within the target region, not on the reflector installation.

4. The method of claim 2, wherein the illumination source is a broadband source, such that the beam of illumination has a spectral bandwidth spanning a plurality of spectral features of the one or more compounds of interest.

5. The method of claim 4, wherein the illumination source is a broadband short-wave infrared (SWIR) source.

6. The method of claim 2, comprising scanning the ifov of the optical sensor across the portion of the reflector installment in a synchronized fashion with the beam of illumination and detecting, within the one or more spectral bands of interest, with the one or more detectors, the light reflected from each of the sampled locations along the reflector installation as the ifov is scanned.

7. The method of claim 1, wherein step (b) comprises detecting light from a plurality of image locations within a target region, wherein the target region comprises the reflector installation and the image locations comprise the plurality of sampled locations on the reflector installation, as well as other locations within the target region, not on the reflector installation.

8. The method of claim 1, wherein the reflector installment comprises one or more continuous reflective sections each comprising a plurality of individual retro-reflective elements.

9. The method of claim 1, wherein the one or more detectors comprise an array detector comprising a plurality of pixels and aligned to image a spatial region comprising two or more of the sampled locations.

10. The method of claim 1, wherein the optical sensor is positioned within 100 meters of a furthest portion of the reflector installation.

11. The method of claim 1, wherein for each of one or more of the sampled locations along the reflector installment, an angle of incidence and/or exitence from a line of sight from the optical sensor to the sampled location along the reflector installation is greater than 1 degree.

12. The method of claim 1, wherein the reflector installment comprises one or more reflective surfaces, each having a minimum dimension sufficiently large to span, for each of the one or more detectors of the optical sensor, a projection of an individual ifov of the detector onto the reflective surface.

13. The method of claim 12, comprising over-sampling the sensor ifov along at least one dimension of each of the one or more reflective surfaces.

14. The method of claim 1, wherein the one or more spectral bands of interest are within the short-wave infrared (SWIR) spectrum.

15. The method of claim 1, wherein each of at least a portion of the one or more spectral bands of interest span an extended spectral feature, comprising a plurality of absorption lines of the one or more compounds of interest.

16. The method of claim 1, wherein at least a portion of the one or more continuous reflective sections comprise at least one of: (i) retroreflective tape, (ii) retroreflective paint, and (iii) a retroreflective blanket on a pre-existing structure.

17. The method of claim 1, wherein the one or more assets to be monitored comprise a storage tank and/or a separator.

18. A system for detecting emission of gas comprising one or more compounds of interest, the system comprising:
(a) a reflector installation mounted about a site to be monitored, wherein the reflector installation comprises one or more continuous reflective sections, wherein each continuous reflective section: (i) comprises a retroreflective panel mounted on and/or retroreflective material affixed to a pre-existing structure in proximity to and behind, with respect to a location of the optical sensor, one or more assets to be monitored for gas emission, (ii) is oriented vertically with respect to a plane passing through the optical sensor and above the site, and (iii) is of sufficient size to span a plurality of sampled locations;
(b) an optical sensor positioned in proximity to the reflector installation comprising one or more detectors, wherein:
the one or more detectors are aligned and operable to detect light within one or more spectral bands of interest, at least a portion of said spectral bands of interest overlapping with one or more spectral features associated with the one or more compounds of interest, and
the one or more detectors are aligned to detect light reflected from a plurality of sampled locations on the reflector installation and captured within an instantaneous field of view (ifov) of the optical sensor;
(c) a processor of a computing device; and
(d) a memory having instructions stored thereon, wherein the instructions, when executed by one processor, cause the processor to:
receive and/or access, data corresponding to the detected light from each of the plurality of sampled locations;
determine, for each of the plurality of sampled locations, an absorption level associated with at least one of the one or more spectral features using the detected light, thereby generating a spectral absorption map comprising a plurality of absorption levels, each associated with a particular sampled location and spectral feature; and
detect the emission of the gas from with the site to be monitored using the generated spectral absorption map.

19. The system of claim 18, comprising a scanning illuminator aligned and operable to emit and direct a structured illumination beam towards the reflector installation and scan the structured illumination beam across at least a portion of the reflector installation, thereby illuminating the plurality of sampled locations.

20. The system of claim 19, wherein the scanning illuminator is operable to scan the beam of illumination in a continuous fashion across a portion of a target region comprising the reflector installation, thereby illuminating the plurality of sampled locations along the reflector installment as well as other locations within the target region, not on the reflector installation.

21. The system of claim 19, wherein the scanning illuminator is a broadband source, such that the beam of illumination has a spectral bandwidth spanning a plurality of spectral features of the one or more compounds of interest.

22. The system of claim 21, wherein the scanning illuminator comprises a broadband short-wave infrared (SWIR) source.

23. The system of claim 19, comprising an optical sensor scanner operable to scan the ifov of the optical sensor across the portion of the reflector installment in a synchronized fashion with the beam of illumination and so as to detect, with the one or more detectors, within the one or more spectral bands of interest, the light reflected from each of the sampled locations along the reflector installment as the ifov is scanned.

24. The system of claim 18, comprising an optical sensor scanner operable to scan the ifov of the optical sensor across at least a portion of the reflector installment, so as to detect, with the one or more detectors, within the one or more spectral bands of interest, light reflected from each of the sampled locations along the reflector installment as the ifov is scanned.

25. The system of claim 18, wherein the reflector installment comprises one or more continuous reflective sections each comprising a plurality of individual retro-reflective elements.

26. The system of claim 18, wherein the one or more detectors comprise an array detector comprising a plurality of pixels and aligned to image a spatial region comprising two or more of the sampled locations.

27. The system of claim 18, wherein the optical sensor is positioned within 100 meters of a furthest portion of the reflector installment.

28. The system of claim 18, wherein for each of one or more of the sampled locations along the reflector installment, an angle of incidence and/or exitence from a line of sight from the optical sensor to the sampled location along the reflector installment is greater than 1 degree.

29. The system of claim 18, wherein the reflector installment comprises one or more reflective surfaces, each having a minimum dimension sufficiently large to span, for each of the one or more detectors of the optical sensor, a projection of an individual ifov of the detector onto the reflective surface.

30. The system of claim 29, comprising an optical sensor scanner operable to scan the sensor ifov in a manner that over-samples along at least one dimension of each of the one or more reflective surfaces.

31. The system of claim 18, wherein the one or more spectral bands of interest are within the short-wave infrared (SWIR) spectrum.

32. The system of claim 18, wherein each of at least a portion of the one or more spectral bands of interest span an extended spectral feature, comprising a plurality of absorption lines of the one or more compounds of interest.

33. The system of claim 18, wherein at least a portion of the one or more continuous reflective sections comprise at least one of: (i) retroreflective tape, (ii) retroreflective paint, and (iii) a retroreflective blanket on a pre-existing structure.

34. The system of claim 33, wherein each retroreflective section extends along at least 10% of a perimeter of the asset.

35. The system of claim 18, wherein the one or more assets to be monitored comprise a storage tank and/or a separator.

36. A system for detecting emission of gas comprising one or more compounds of interest, the system comprising:
(a) a reflector installment mounted about a site to be monitored, wherein the reflector installment comprises one or more continuous retroreflective panels and/or surfaces covered in retroreflective material, each mounted along a portion of an edge of an asset to be monitored, extending upwards with respect to a top of the asset, and oriented behind the asset with respect to an observation point at a location of the optical sensor;
(b) an optical sensor positioned in proximity to the reflector installment comprising one or more detectors, wherein:
the one or more detectors are aligned and operable to detect light within one or more spectral bands of interest, at least a portion of said spectral bands of interest overlapping with one or more spectral features associated with the one or more compounds of interest, and
the one or more detectors are aligned to detect light reflected from a plurality of sampled locations on the reflector installment and captured within an instantaneous field of view (ifov) of the optical sensor;
(c) a processor of a computing device; and
(d) a memory having instructions stored thereon, wherein the instructions, when executed by one processor, cause the processor to:
receive and/or access, data corresponding to the detected light from each of the plurality of sampled locations;
determine, for each of the plurality of sampled locations, an absorption level associated with at least one of the one or more spectral features using the detected light, thereby generating a spectral absorption map comprising a plurality of absorption levels, each associated with a particular sampled location and spectral feature; and
detect the emission of the gas from with the site to be monitored using the generated spectral absorption map.

37. A system for detecting emission of gas comprising one or more compounds of interest, the system comprising:
(a) a reflector installment mounted about a site to be monitored, wherein the reflector installment comprises one or more vertical posts having retroreflective surfaces comprising continuous sections of sufficient size to span a plurality of sampled locations;
(b) an optical sensor positioned in proximity to the reflector installment comprising one or more detectors, wherein:
the one or more detectors are aligned and operable to detect light within one or more spectral bands of interest, at least a portion of said spectral bands of interest overlapping with one or more spectral features associated with the one or more compounds of interest, and
the one or more detectors are aligned to detect light reflected from a plurality of sampled locations on the reflector installment and captured within an instantaneous field of view (ifov) of the optical sensor;
(c) a processor of a computing device; and
(d) a memory having instructions stored thereon, wherein the instructions, when executed by one processor, cause the processor to:
receive and/or access, data corresponding to the detected light from each of the plurality of sampled locations;
determine, for each of the plurality of sampled locations, an absorption level associated with at least one of the one or more spectral features using the detected light, thereby generating a spectral absorption map comprising a plurality of absorption levels, each associated with a particular sampled location and spectral feature; and detect the emission of the gas from with the site to be monitored using the generated spectral absorption map.

38. The system of claim 37, wherein the one or more posts are relocatable.

39. A system for detecting emission of gas comprising one or more compounds of interest, the system comprising:

(a) a reflector installment mounted about a site to be monitored, wherein the reflector installment comprises a frame comprising one or more vertical posts and horizontal crossbars having retroreflective surfaces, the frame at least partially encircling a boundary of a region comprising an asset to be monitored for gas emission and mounted behind the asset with respect to an observation point at a location of the optical sensor;

(b) an optical sensor positioned in proximity to the reflector installment comprising one or more detectors, wherein:

the one or more detectors are aligned and operable to detect light within one or more spectral bands of interest, at least a portion of said spectral bands of interest overlapping with one or more spectral features associated with the one or more compounds of interest, and the one or more detectors are aligned to detect light reflected from a plurality of sampled locations on the reflector installment and captured within an instantaneous field of view (ifov) of the optical sensor;

(c) a processor of a computing device; and (d) a memory having instructions stored thereon, wherein the instructions, when executed by one processor, cause the processor to:

receive and/or access, data corresponding to the detected light from each of the plurality of sampled locations;

determine, for each of the plurality of sampled locations, an absorption level associated with at least one of the one or more spectral features using the detected light, thereby generating a spectral absorption map comprising a plurality of absorption levels, each associated with a particular sampled location and spectral feature; and detect the emission of the gas from with the site to be monitored using the generated spectral absorption map.

* * * * *